(12) United States Patent
Gelfuso

(10) Patent No.: US 7,325,920 B1
(45) Date of Patent: Feb. 5, 2008

(54) GLASSES FOR MOUNTING TO BOTH REARWARD AND FORWARD FACING CAPS

(76) Inventor: Russell Gelfuso, 1304 New London Ave., Cranston, RI (US) 02920

( * ) Notice: Subject to any disclaimer, the term of this patent is extended or adjusted under 35 U.S.C. 154(b) by 0 days.

(21) Appl. No.: 11/803,041

(22) Filed: May 11, 2007

Related U.S. Application Data

(63) Continuation-in-part of application No. 11/325,878, filed on Jan. 5, 2006, now Pat. No. 7,216,972.

(51) Int. Cl.
G02C 5/22 (2006.01)
A61F 9/00 (2006.01)

(52) U.S. Cl. .............. 351/155; 2/10; 2/452; 2/453
(58) Field of Classification Search ........... 351/155, 351/156, 158, 41; 2/10, 452, 453, 12, 13
See application file for complete search history.

(56) References Cited

U.S. PATENT DOCUMENTS

| 4,781,451 | A | * | 11/1988 | McAllen | 351/156 |
|---|---|---|---|---|---|
| 5,966,738 | A | * | 10/1999 | Wang Lee | 2/10 |
| 6,595,635 | B2 | * | 7/2003 | Schubert | 351/155 |
| 6,892,393 | B1 | * | 5/2005 | Provost et al. | 2/10 |
| 7,216,972 | B1 | * | 5/2007 | Gelfuso | 351/155 |

* cited by examiner

Primary Examiner—Hung Xuan Dang
(74) Attorney, Agent, or Firm—Robert J Doherty

(57) ABSTRACT

Glasses adapted to be mounted on caps having an interior band such that terminal temple connecting portions are mounted on such band at two circumferentially-spaced positions, and the glasses so mounted are further adapted to upwardly pivot such that the glasses are easily utilized with caps worn in both the brim rearward and forward positions and wherein the temple connecting portions include means for limited relative rotation therebetween.

15 Claims, 28 Drawing Sheets

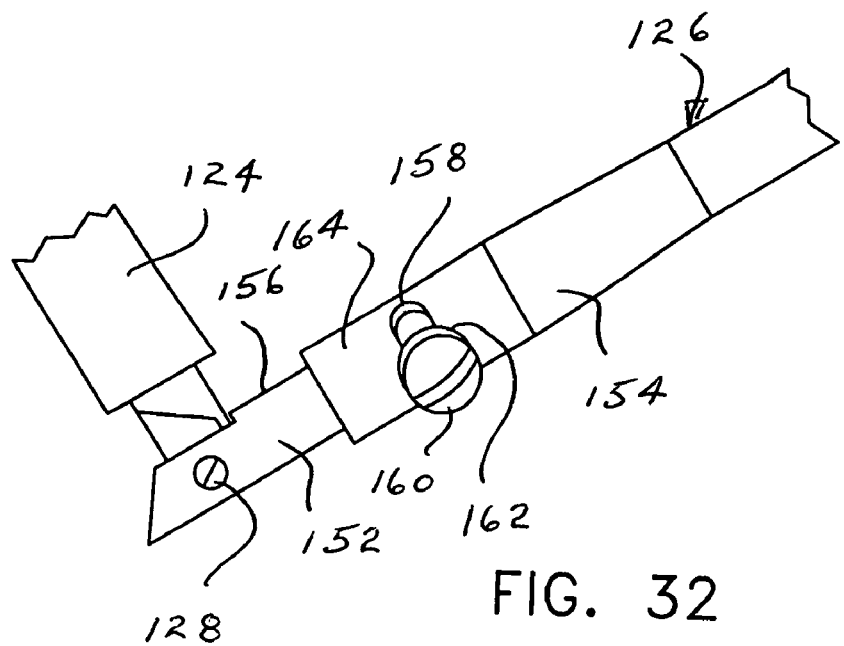
FIG. 32
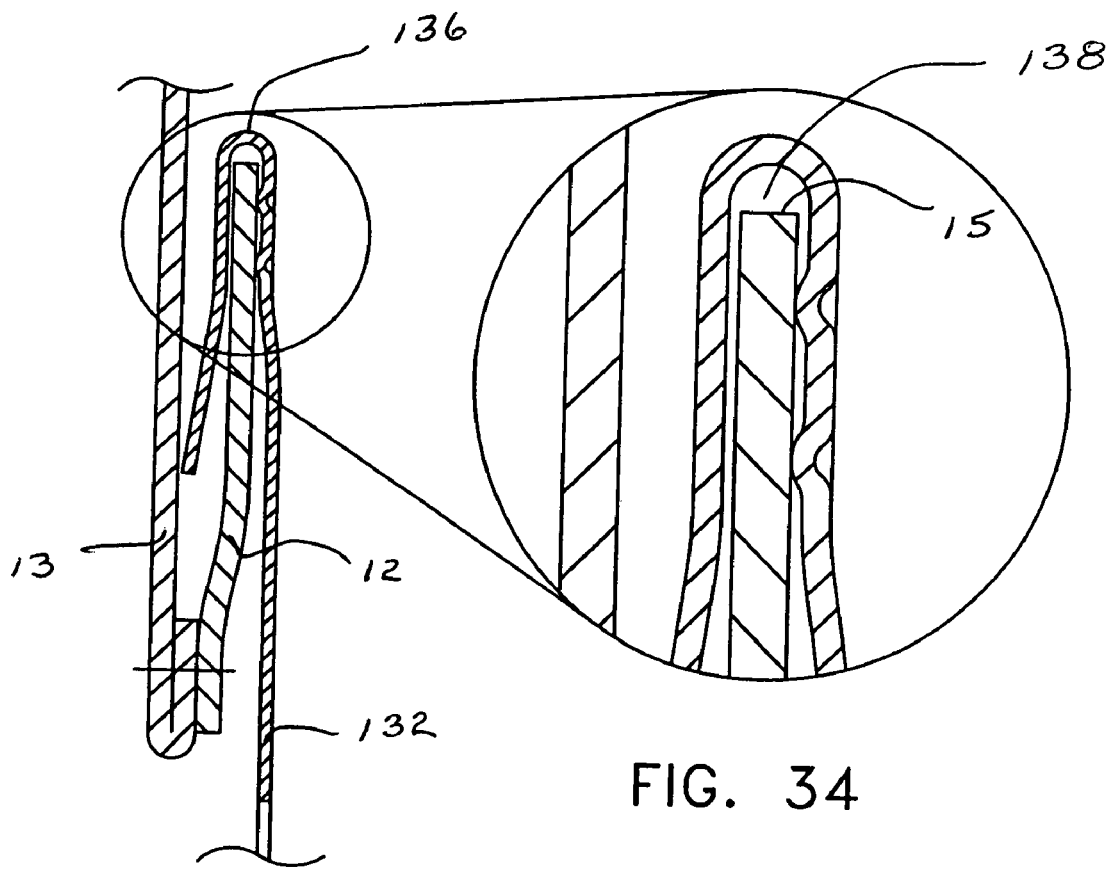
FIG. 34
FIG. 33

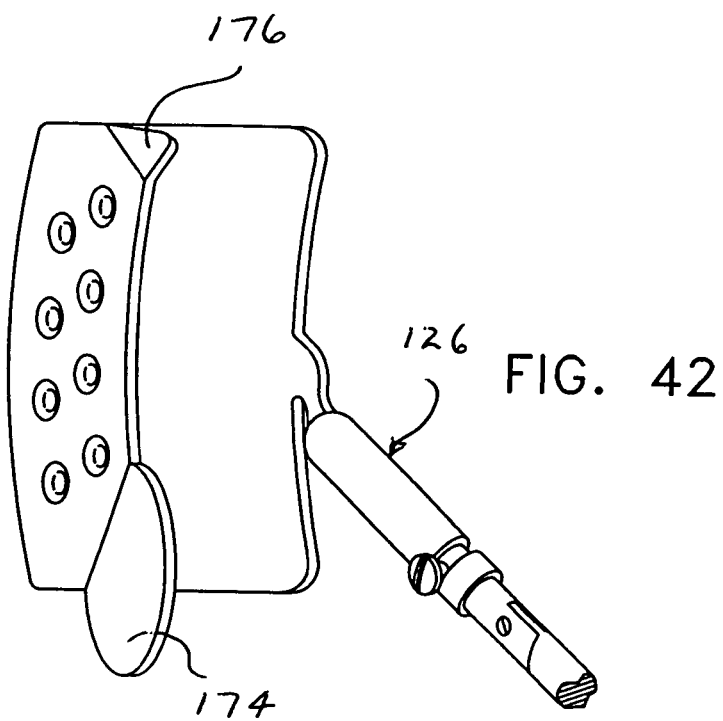
FIG. 42
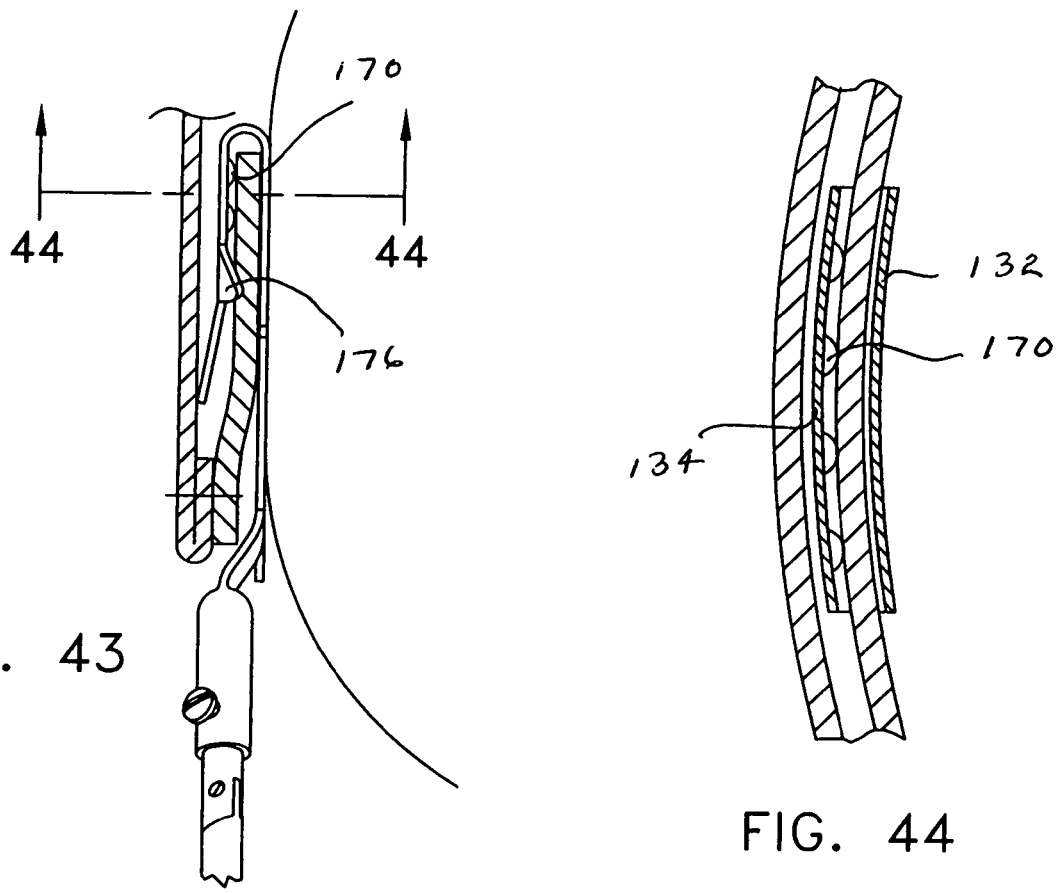
FIG. 43
FIG. 44

GLASSES FOR MOUNTING TO BOTH REARWARD AND FORWARD FACING CAPS

This application is a Continuation-In-Part of Ser. No. 11/325,878 filed Jan. 5, 2006 now U.S. Pat. No. 7,216,972 issued May 15, 2007.

BACKGROUND OF THE INVENTION

This invention relates to a pair of glasses adapted to be attached to caps worn by humans and more specifically for utilization when caps are worn backwards, that is, with the cap's brim or visor facing to the rear. Visored caps such as baseball caps and the like have realized increased acceptance and importance in today's culture, and the habit of wearing such caps in the rearward position, that is, with the visor portion placed to the rear, is popular. It is also popular to mount eyeglasses, safety glasses and sunglasses to such caps such that the glasses may be disposed in a storage position and then pivoted or otherwise disposed to a use position with respect to the wearer, i.e., combination visored cap with glasses mounted thereon.

Despite the popularity of wearing such visored caps in the rearward position, the construction of the glasses to be mounted thereon are almost entirely structured so as to be clipped, suspended or otherwise attached or function with respect to the cap's brim or visor. Thus mounted, the glasses so attached to the cap will, of course, be proximate to the rear of the person's head when the cap is disposed in the rearward position and thus rendering the functionality of such mounted glasses useless. Examples of such visor or brim-oriented glasses/cap mountings include those shown in the following U.S. Pat. Nos. 857,838 issued Jun. 25, 1907; 4,179,753 issued Dec. 25, 1979; 5,052,054 issued Oct. 1, 1991; 5,615,413 issued Apr. 1, 1997; 5,933,862 issued Aug. 10, 1999; 6,739,718 issued May 24, 2004; and 6,757,914 issued Jul. 6, 2004.

While some attempts have been made to provide glasses which include some attachment mechanism to enable use while the hat or cap's brim faces to the back or towards either side, the need still exists for a pair of glasses adapted for attachment to a cap such that the wearer may utilize the glasses when the cap is worn in the rearward facing position in a simple, straightforward and intuitively functional manner.

SUMMARY OF THE INVENTION

Accordingly, a primary object of this invention is to allow users to instantly attach and detach their choice of sunglasses, safety glasses and prescription eyeglasses to any headwear with an interior band such as a baseball-type cap such that the cap can be comfortably worn with the brim facing in any direction.

Another object of this invention is to improve comfort by eliminating contact by the glasses with the wearer's ears and hinged temples that wrap around the wearer's ears as shown in prior art.

An additional object of this invention is to prevent the eyeglass frames from irritating the wearer by sliding down the nose by eliminating the traditional nosepieces as shown in prior art.

An additional object of this invention is to provide safe storage of the glasses when they are not in use without having to carry them.

A further object of this invention is to attach a pair of eyeglasses to the hat or cap in a manner that does not alter or damage the cap in any way.

A still further object of this invention is to provide the wearer's eyes protection from the sun by the lenses even when the cap is being worn with the brim facing in any position other than toward the front.

These and other objects of the invention are accomplished by the provision of a pair of eyeglasses having a frame and a pair of temple members rearwardly extending therefrom and wherein each said temple members terminate in an end portion adapted to attach to the inner band of the cap at spaced circumferential portions thereof and wherein the main temple portions are hingedly connected to the temple attachment portion.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 32 is an enlarged partial view of FIG. 31;

FIG. 33 is an enlarged sectional view along the line 33-33 of FIG. 31;

FIG. 34 is an enlarged partial view of FIG. 33;

FIG. 42 is another partial perspective view of the connecting flange pair shown in FIG. 40;

FIG. 43 is a side sectional view taken through the headband and illustrating the mounting of the flange pair therein;

FIG. 44 is a sectional view along the line 44-44 in FIG. 43; and

DESCRIPTION OF THE INVENTION

Figure 1:
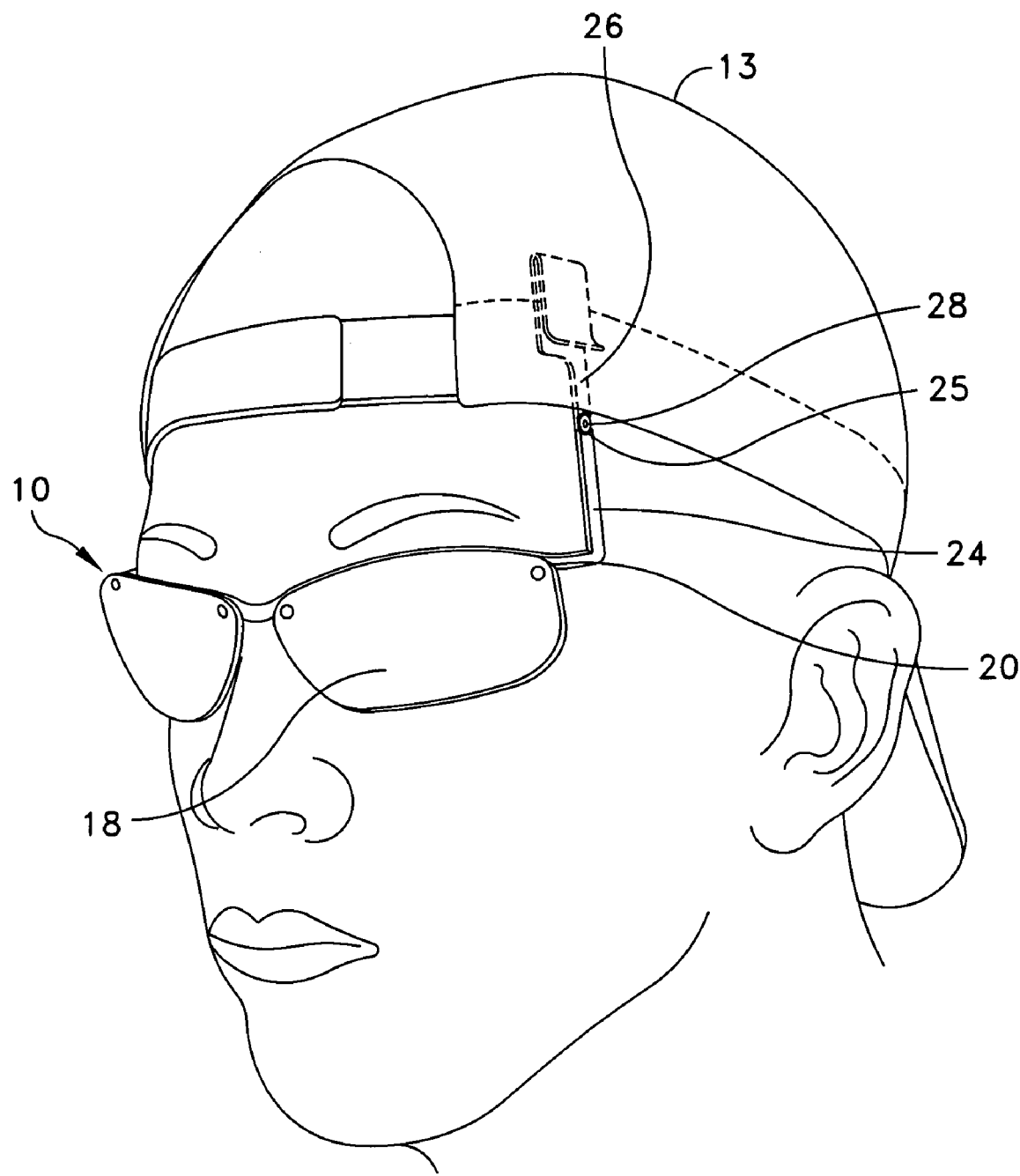
FIG. 1 is a front perspective view showing the glasses of the present invention mounted upon a cap worn backwards and in the active use position.

The glasses 10 of the present invention are depicted in a position mounted to the inner headband 12 of a cap 13. Such headbands 12 generally extend circumferentially about the bottom inside portion of the top 14 of caps 13. The headband may terminate at the rear of the cap to provide for snap or Velcro-type head size adjustment. The glasses 10 include a frame 16 preferably of one-piece anodized aluminum or other suitable material that in turn supports a pair of eyepieces 18 by conventional means such as the rivets 20. Temples 22 are disposed at the lateral ends of the frame. The temples include forward or main temple portions 24 which rearwardly extend from the frame and are, in turn, connected at their ends 25 to rearwardly extending temple portions 26 via a pivot connection 28. The rearward extending portions of the temples 22 in turn each terminate in a connecting or attaching portion 30.

The temple connecting portions 30 include an inner flange 32, that is, an extension of the rearward temple portion 26, and an outwardly positioned flange 34 separated therefrom and connected thereto by a U-shaped bend or web 36. It should be pointed out that the rearwardly extending portion 26 is preferably bent or twisted such that the receiving groove 38 for the band 12 formed between the flanges 32 and 34 is disposed in a somewhat offset position such that the rearwardly extending portion 26 is readily adapted to receive the cap's band 14 without buckling or puckering, etc. The band 12 generally comprises a vertically oriented circumferentially extending fabric which is often the upturned periphery of the cap top 14 and includes a terminal edge 15 over which the groove 38 extends. The outer wall or flange 34 is also outwardly offset at its lower terminal portion 42 to form a lead-in to facilitate the receipt of the band 12.

Figure 2:
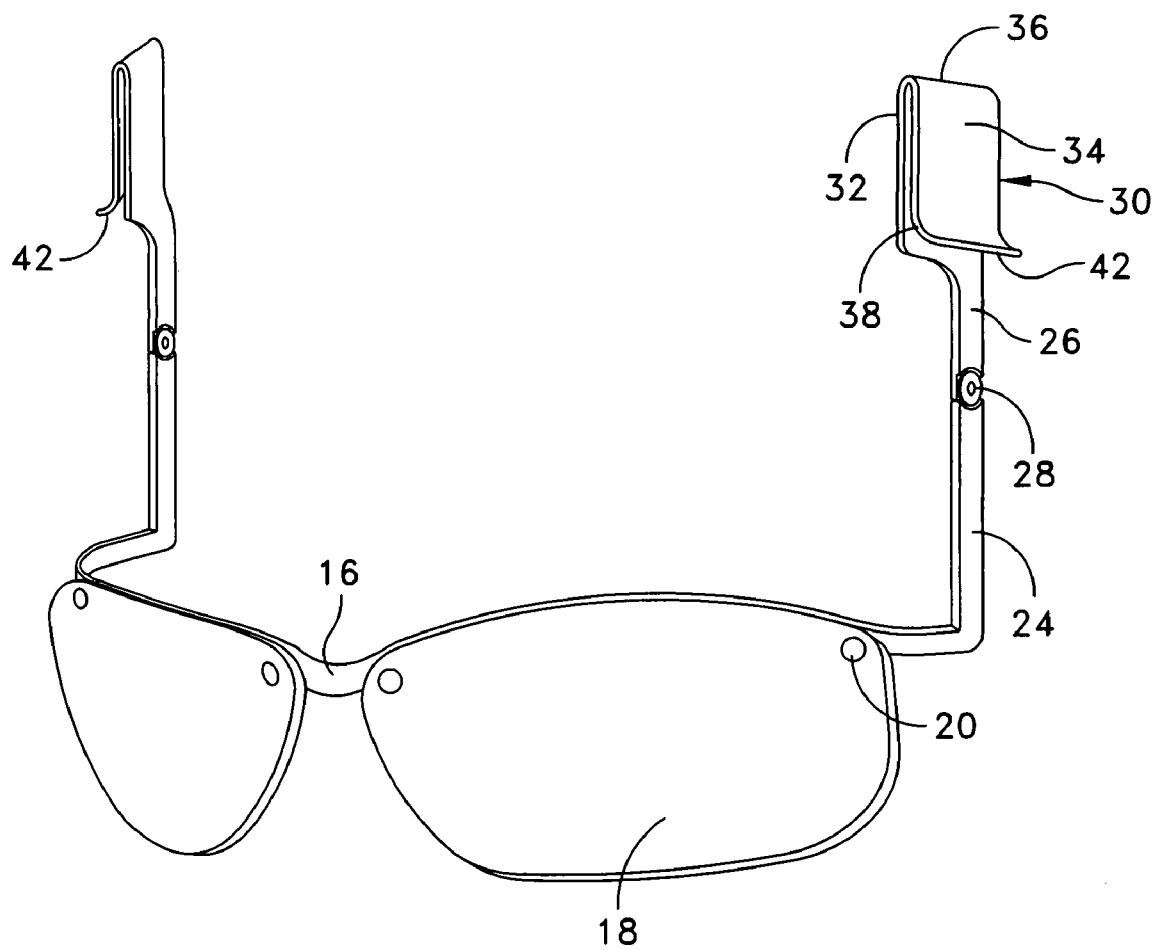
FIG. 2 is a similar perspective view of the glasses showing the temples in a straight mounting position.
Figure 3:
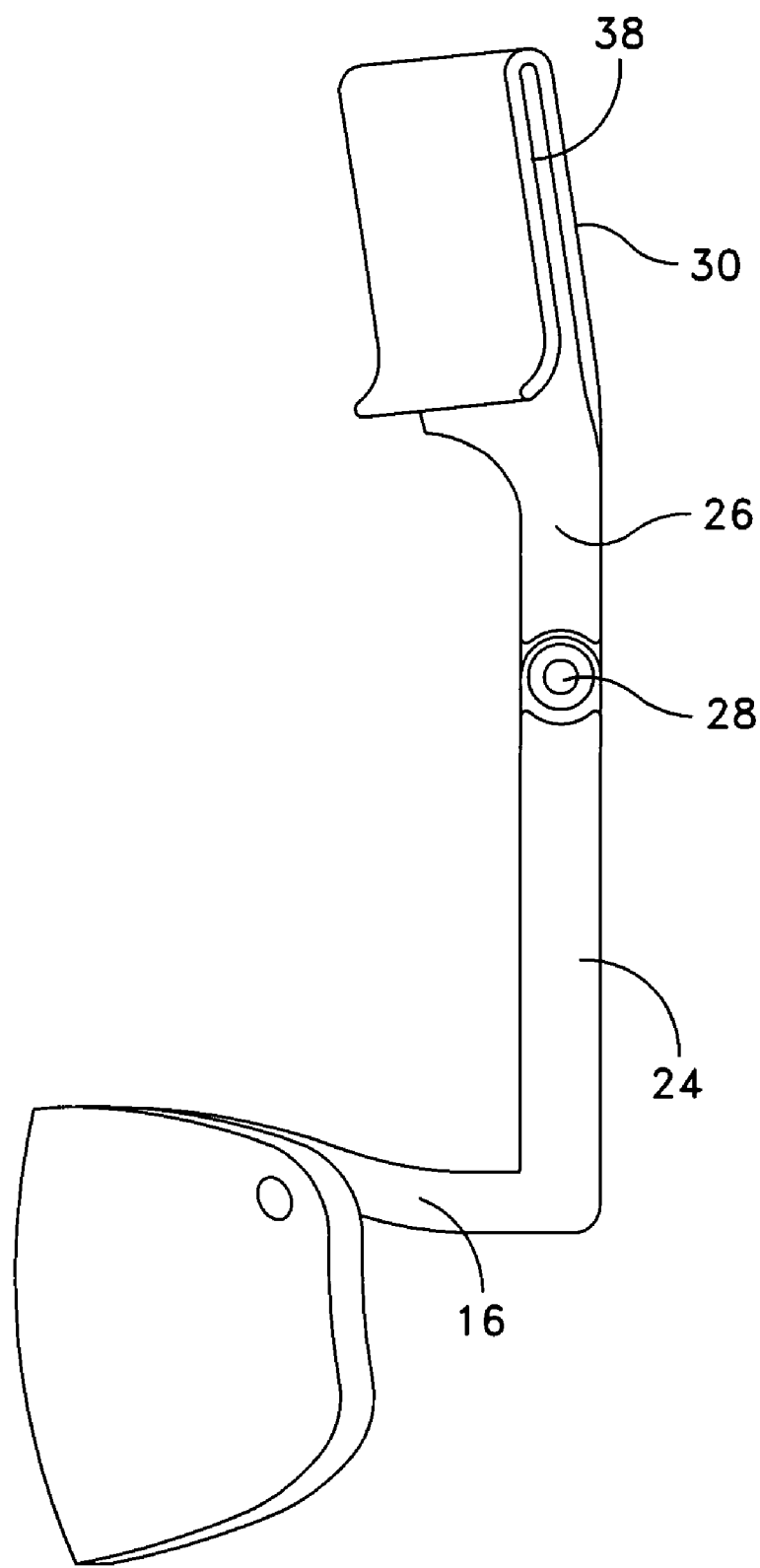
FIG. 3 is a right side elevational view of FIG. 2.
Figure 4:
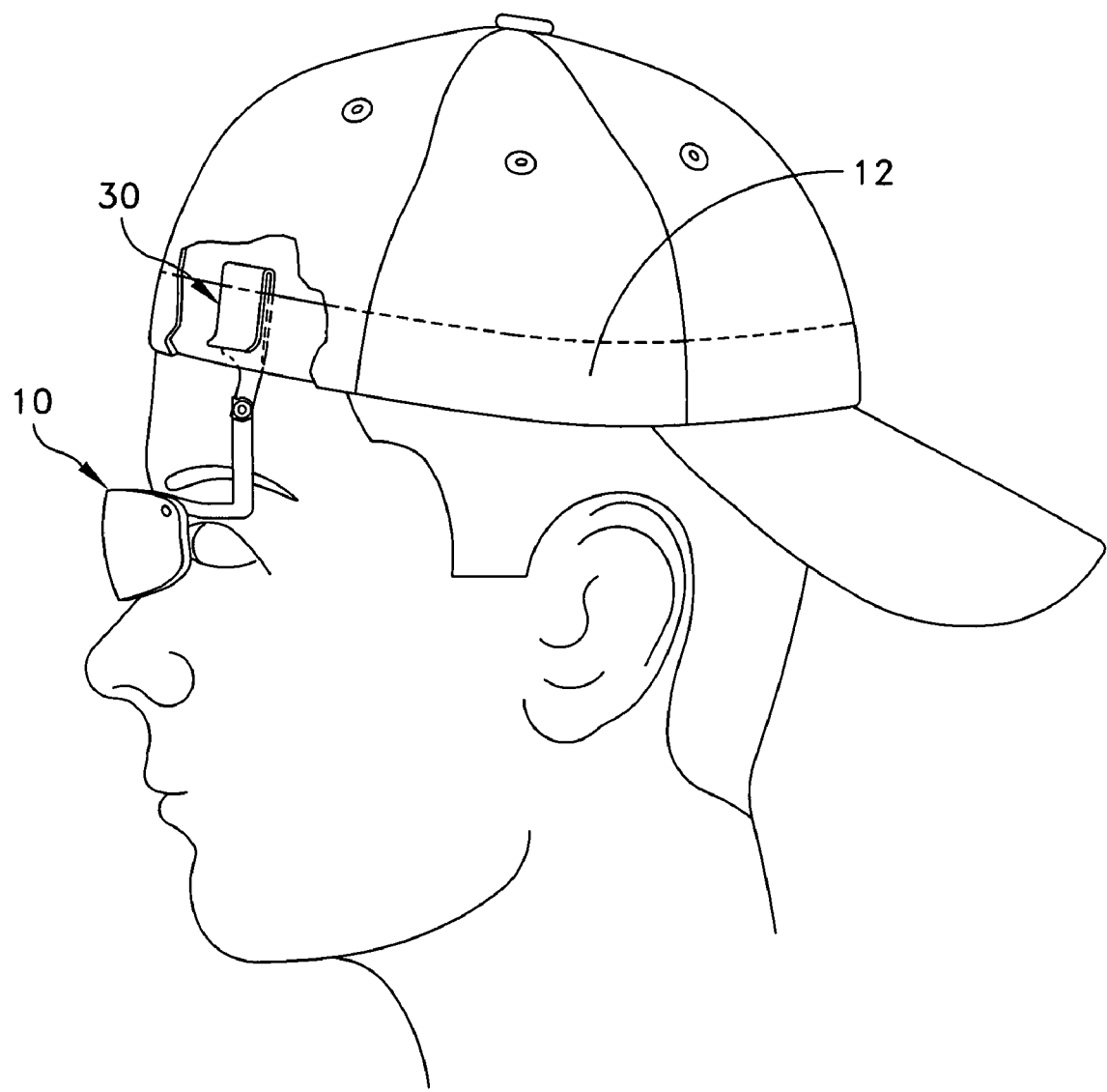
FIG. 4 is a view similar to FIG. 1 but taken from the left side thereof with parts cutaway to show the mounting of the terminal mounting portion of the eyeglass temples to the cap's circumferential inner band.
Figure 5:
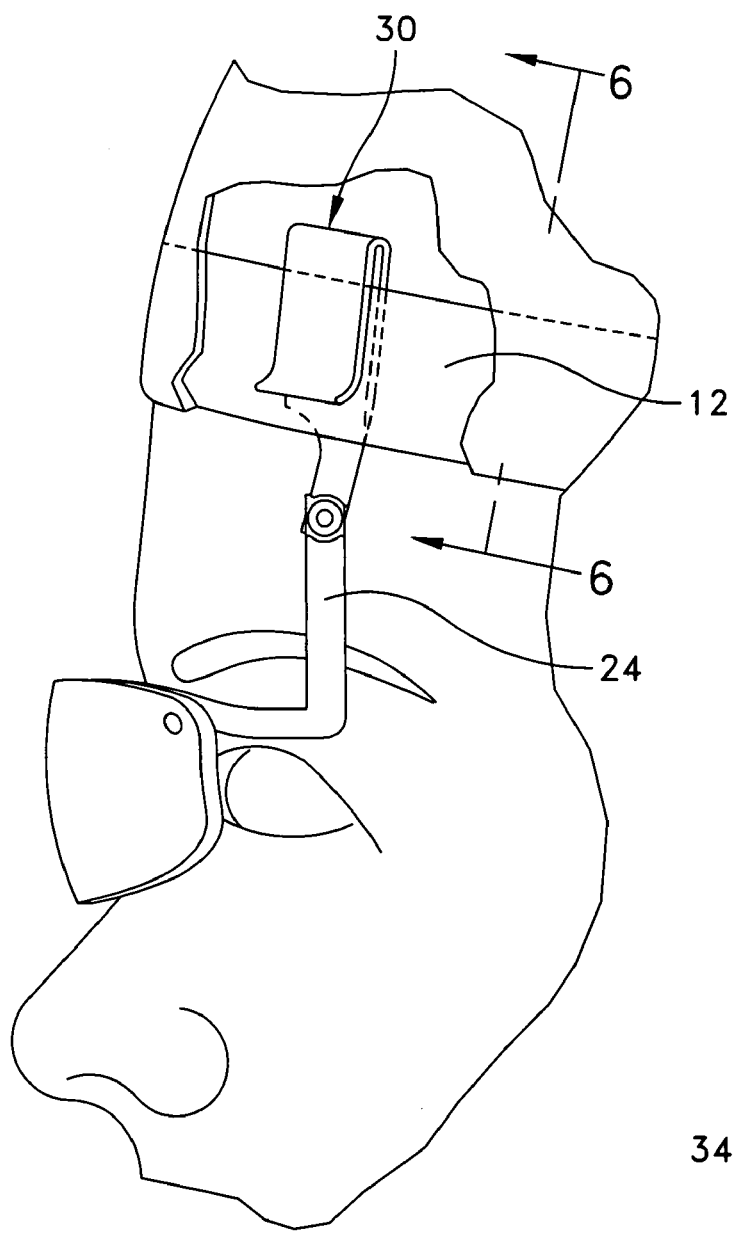
FIG. 5 is an enlarged partial view of FIG. 4.
Figure 6:
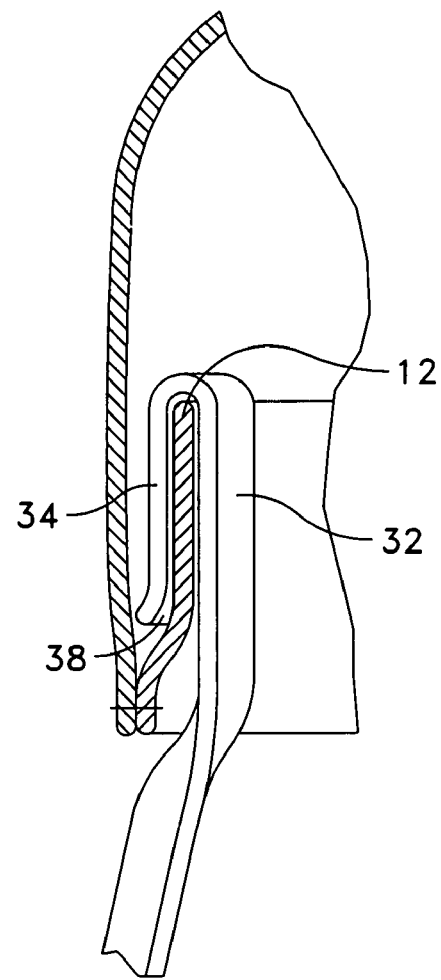
FIG. 6 is a sectional view along the line 6-6 of FIG. 5.

The position of the rearward temple portion 26 is particularly shown in FIG. 2 wherein the rearward temple portion 26 forms a generally straight extension of the forward temple portion 24. This is the position in which the glasses 10 are preferably connected to different circumferentially-spaced portions of the headband 12 by simply placing both of the connector portions 30 into the cap's interior portion proximal the headband and slightly thereabove and then simply moving the glasses downwardly such that the headband is caught between the two flanges 32 and 34. In some cases, the rearward portion or at least the connector portion 30 of the temple 26 may be constructed of a somewhat soft metal such that the flanges 32 and 34 may be squeezed together to assure a tight connection with the headband 12; but in most cases, the groove or slot 38 is dimensioned such that a snug engagement is assured for average width bands 12. In this connection, it should also be brought out that once the cap is placed on one's head then the outer surfaces of the inner flanges 32 rest against the wearer's head and in that way the connecting portions 30 are, in effect, wedged between the cap's circumferential portions and one's head; and in this manner, the glasses are positioned such that they extend in front of the wearer's eyes without the need for a nose piece so as to contacting the wearer's face. The generally wide spacing of the two connection areas along the circumferential extent of the band 12 vis-à-vis the flanges provides a more stable mounting of the glasses such that they can be better manipulated between their use and rest (storage) positions. It should also be pointed out that the lateral extent of either of the flanges 32, 34 may be increased so as to, in effect, create wings as shown by the dotted lines in FIG. 8 so as to increase the flange to band contact and thus the stability of the mounting of the glasses to the cap. Also since there is no reliance upon the visor or brim of the cap 14, the glasses may be worn in the position depicted in FIGS. 1, 4, 5, 7 and 8 without interference from the brim or visor 15, that is, when the cap is worn in a rearward position. Because of the twist of the connectors 30, the grooves or slots 38 are preferably aligned along the path defined by the circumferential disposition of the band 12 at two circumferentially separated connection points.

Figure 7:
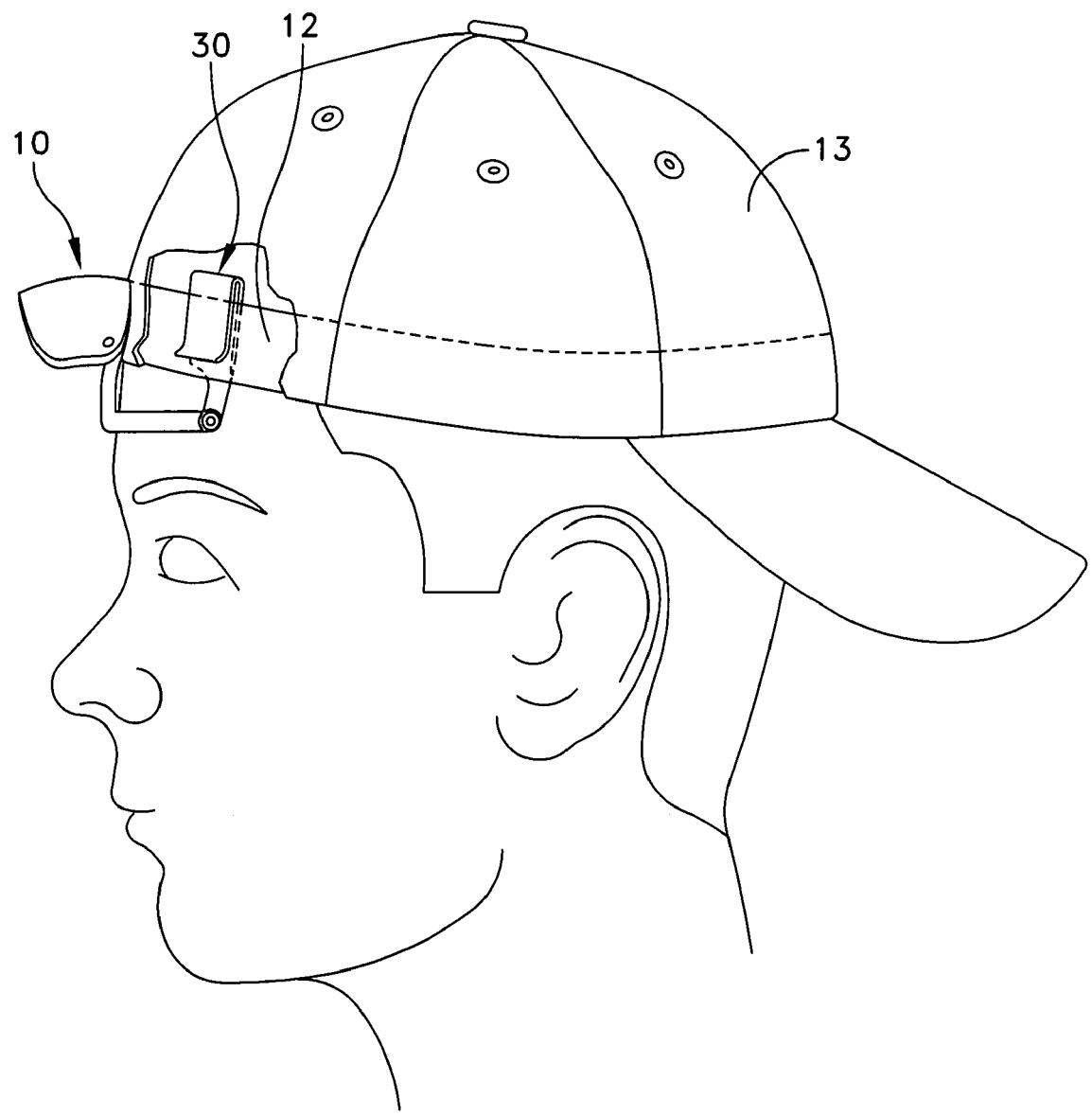
FIG. 7 is a view similar to FIG. 4 but showing the forward main portions of the temples upwardly pivoted to a nonuse/storage position adjacent the cap's rear portion.
Figure 8:
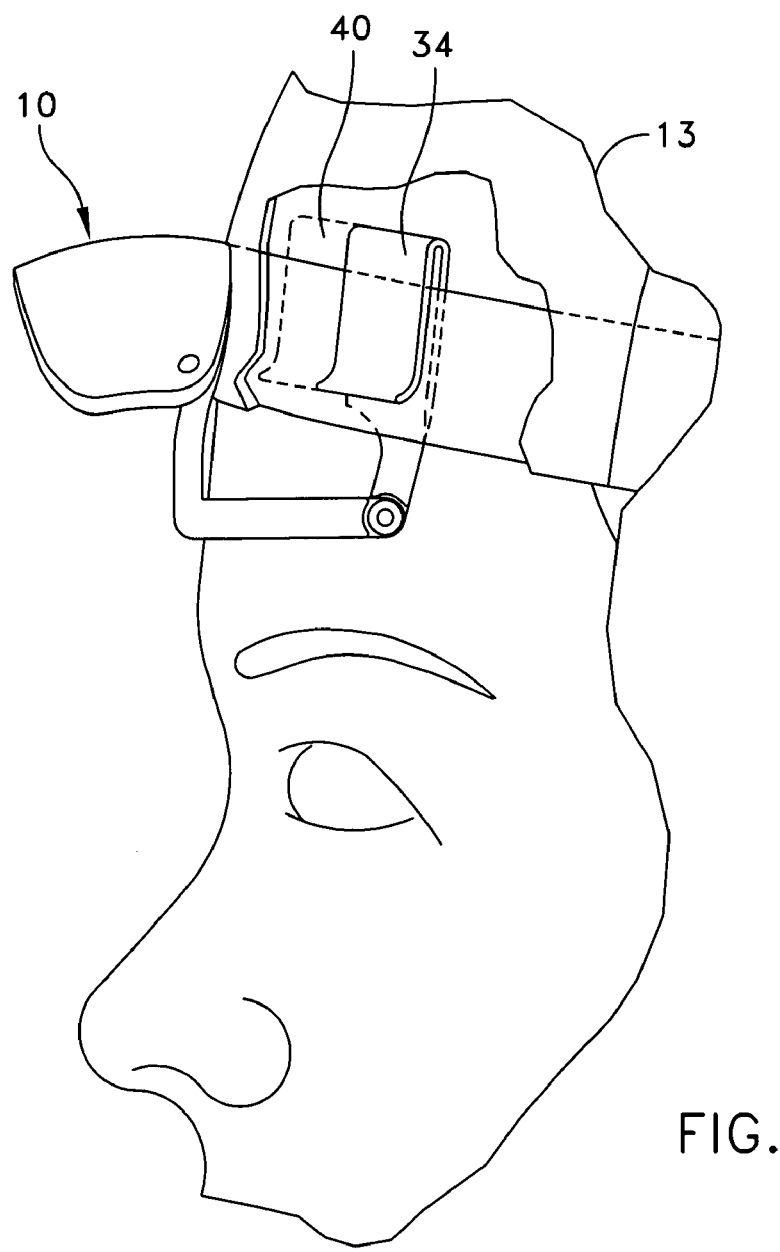
FIG. 8 is an enlarged partial perspective view of FIG. 7.
Figure 9:
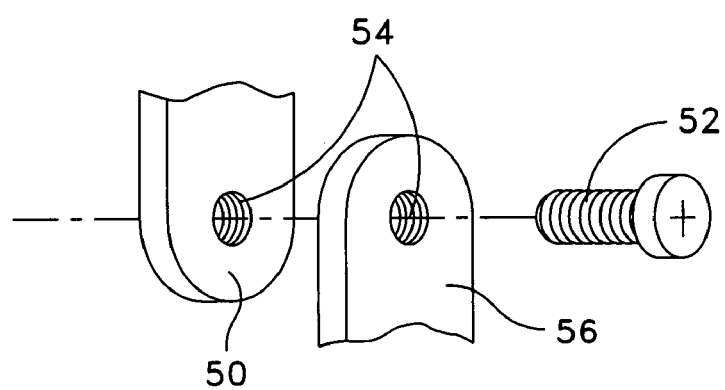
FIG. 9 is a partial perspective view of a pivot connection.

A pivot 28 connects the two temple portions, that is, the forward portion 24 and the rearward portion 26. In its simplest form as shown in FIG. 8 of the drawings, the pivots are formed by a terminal tongue 50 downwardly extending from the rearward extending temple portion 26 and an upwardly extending tongue 52 from the front temple portion 24. The tongues include aligned openings 54 for receipt of a screw or bolt 56 adapted to extend therethrough and connected on the opposite side. Tightening the screw or bolt 56 enables the two tongues to be brought together with a variety of force such that they may be adjusted to enable the temple portions to be pivoted vis-à-vis each other easily or with some degree of desired difficulty. In this way, the lower portion or forward portion temples pivoting about the pivots 28 enable the frame 20 to be upwardly swung to a glasses rest or storage position as best shown in FIGS. 7 and 8. Variations for the pivot connections 28 could be to provide the inner tongue 50 with a threaded opening and utilize a threaded bolt 56 extending through the upwardly extending tongue. Other variations may be provided including providing positive stops to control the relative movement of the lower temple portions 24 and thus the frame 20 about the rear temple portions 26 and the connecting portions positioned within the hat.

Figure 10:
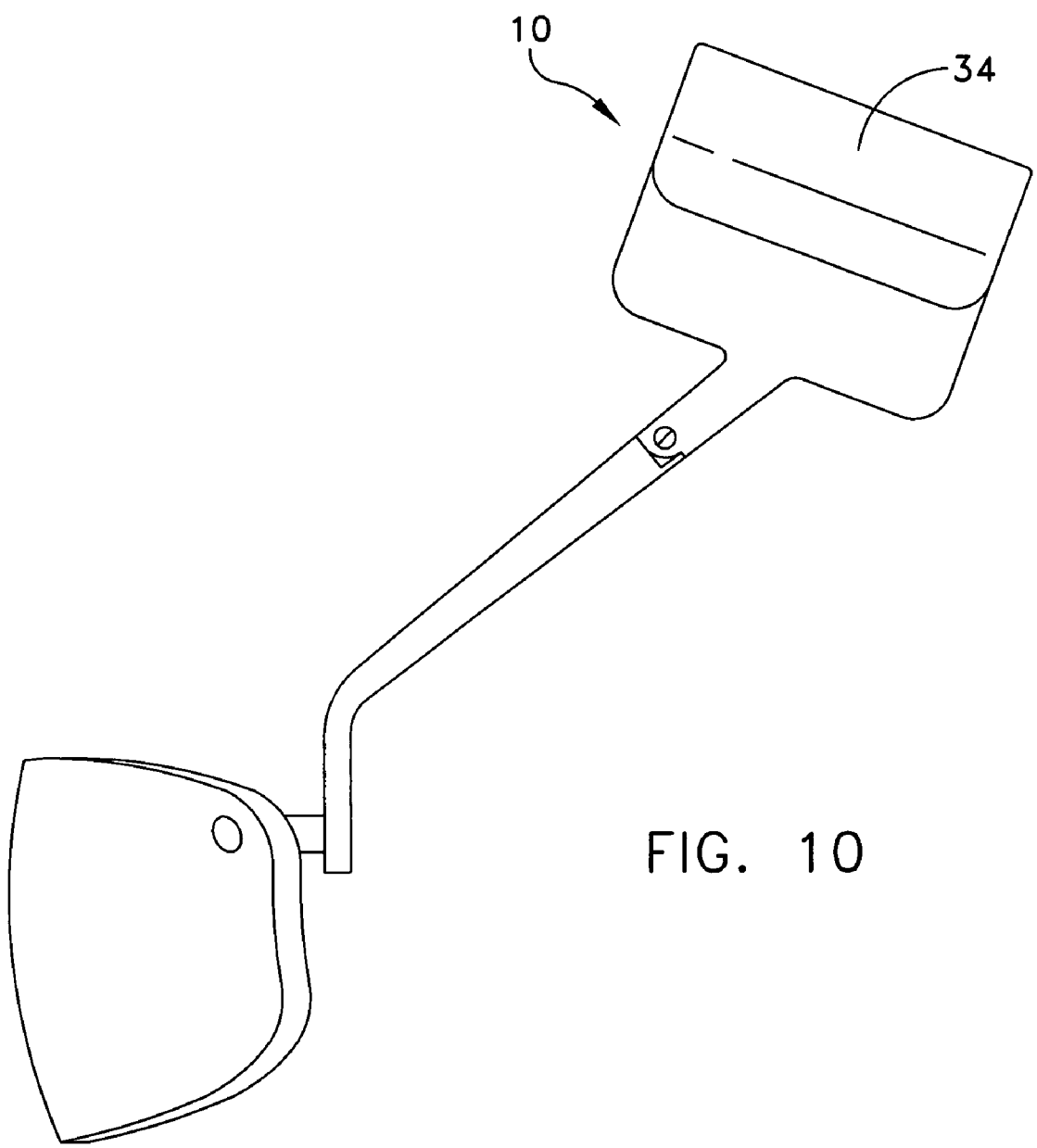
FIG. 10 is a side elevational view of the eyeglasses and the attaching portions wherein the pivot connection is a positive stop type.
Figure 11:
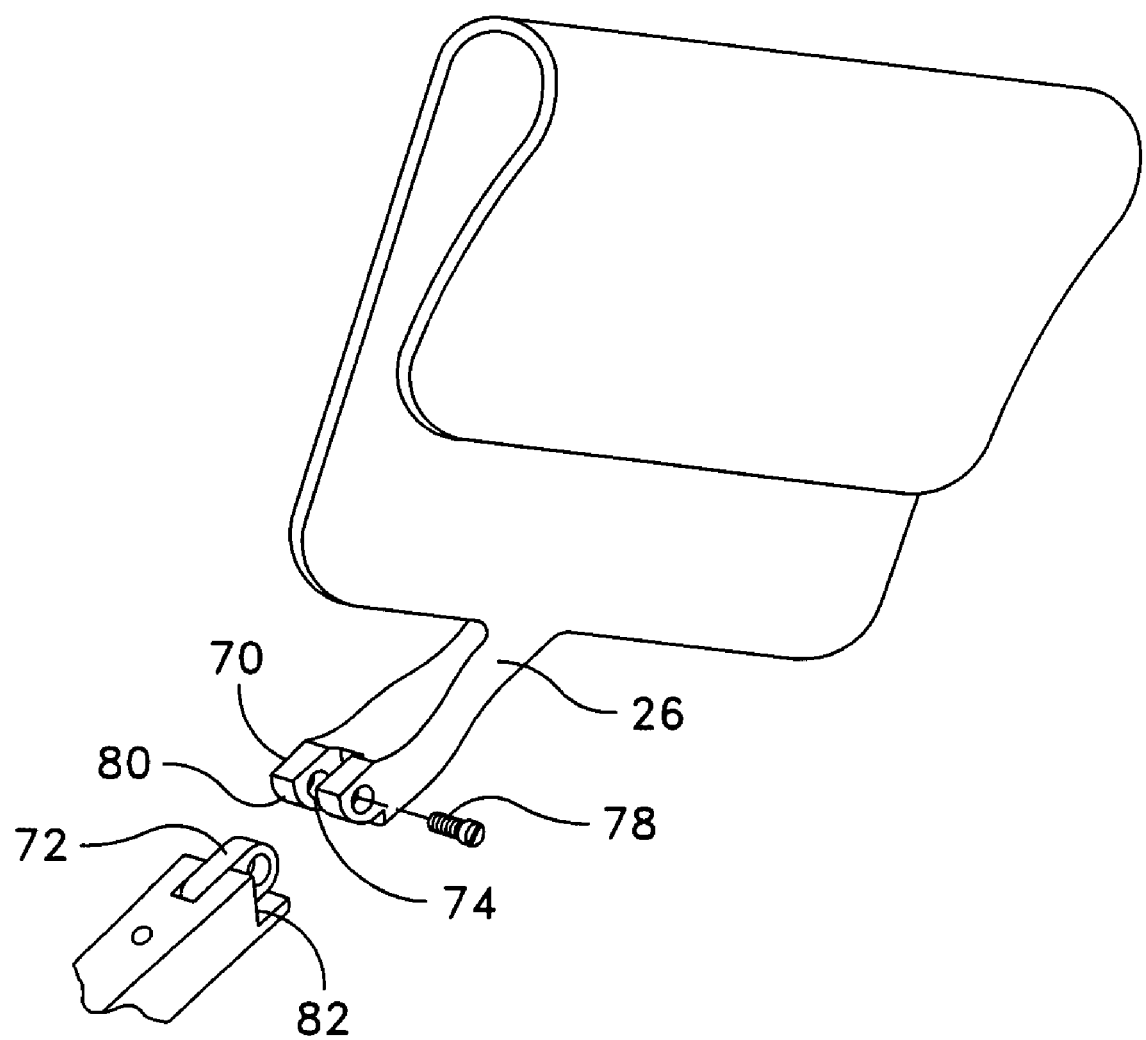
FIG. 11 is a detailed exploded view of the positive stop type pivot connection of FIG. 10.

A modified connecting portion 60 is depicted in FIG. 10 and is of a configuration wherein the lateral extent of the inner and outer flanges 62 and 64 respectively are materially increased so as to increase the contact area between the user's head and the connecting portions via the band 12 on opposite sides of the hat or cap when worn. This larger contact area increases the stability of the glasses when positioned thereon. In addition, the connection between the temple portions 24, 26 includes an angle limiting feature such that the forward temple portion may be pivoted approximately 90 degrees upwardly from the rearward portion 26 to move the glasses attached thereto to their upward storage position.

Figure 12:
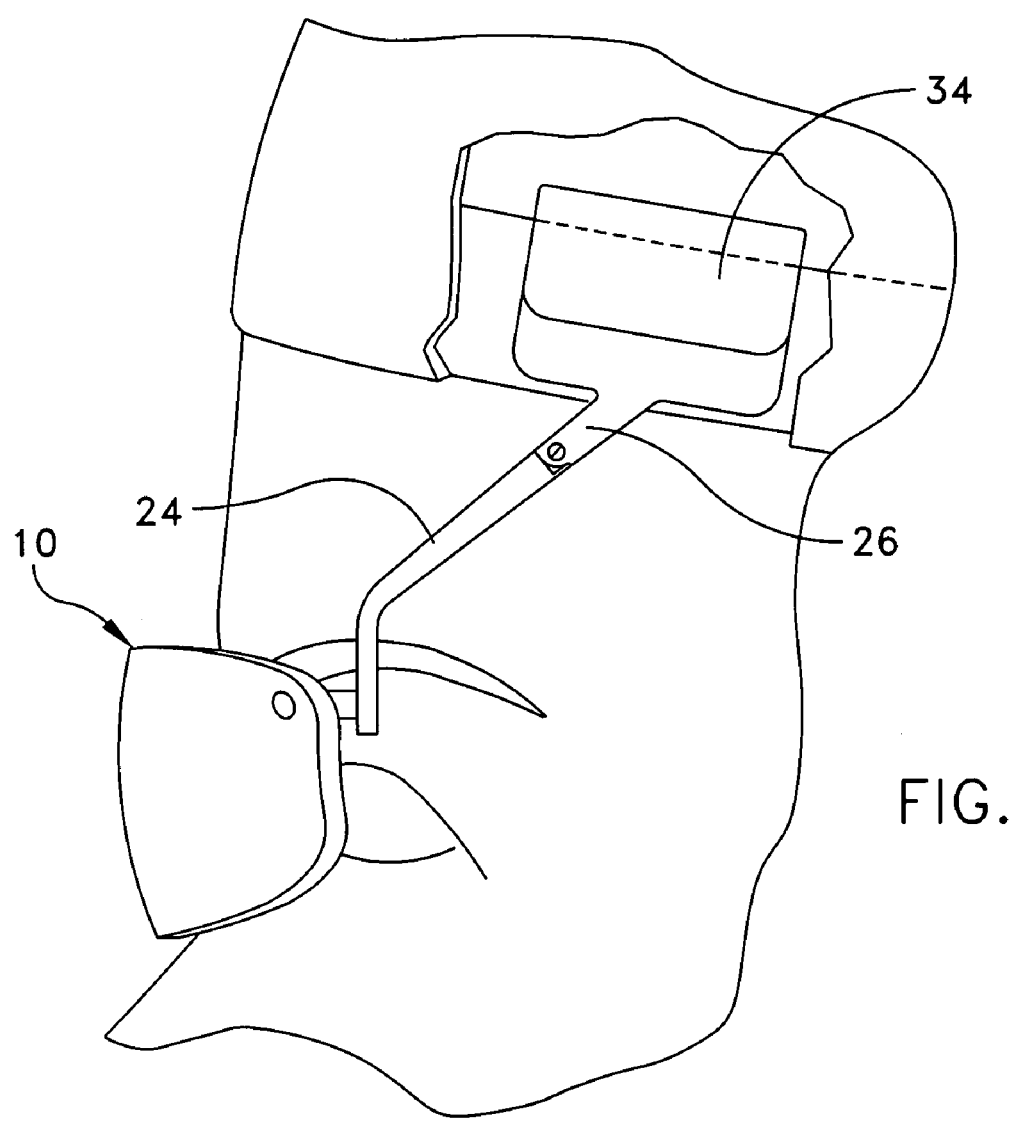
FIG. 12 is a partial side elevational view with parts broken way and showing the eyeglasses and attaching portions mounted on a hat or cap in a rearward facing position.
Figure 13:
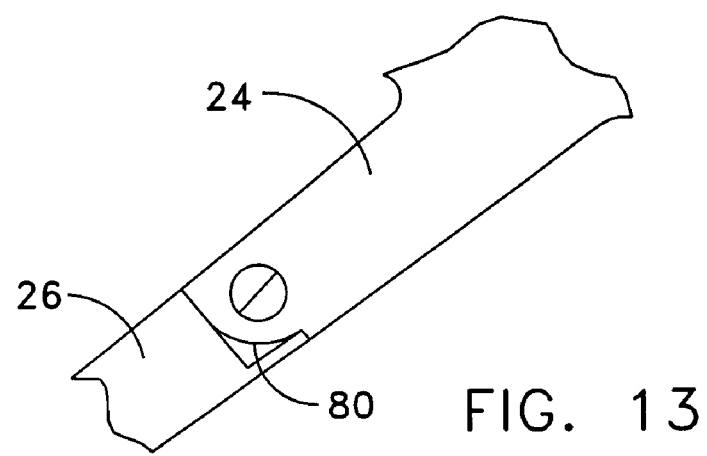
FIG. 13 is a detailed view of a portion of FIG. 12 showing the pivot connection.
Figure 14:
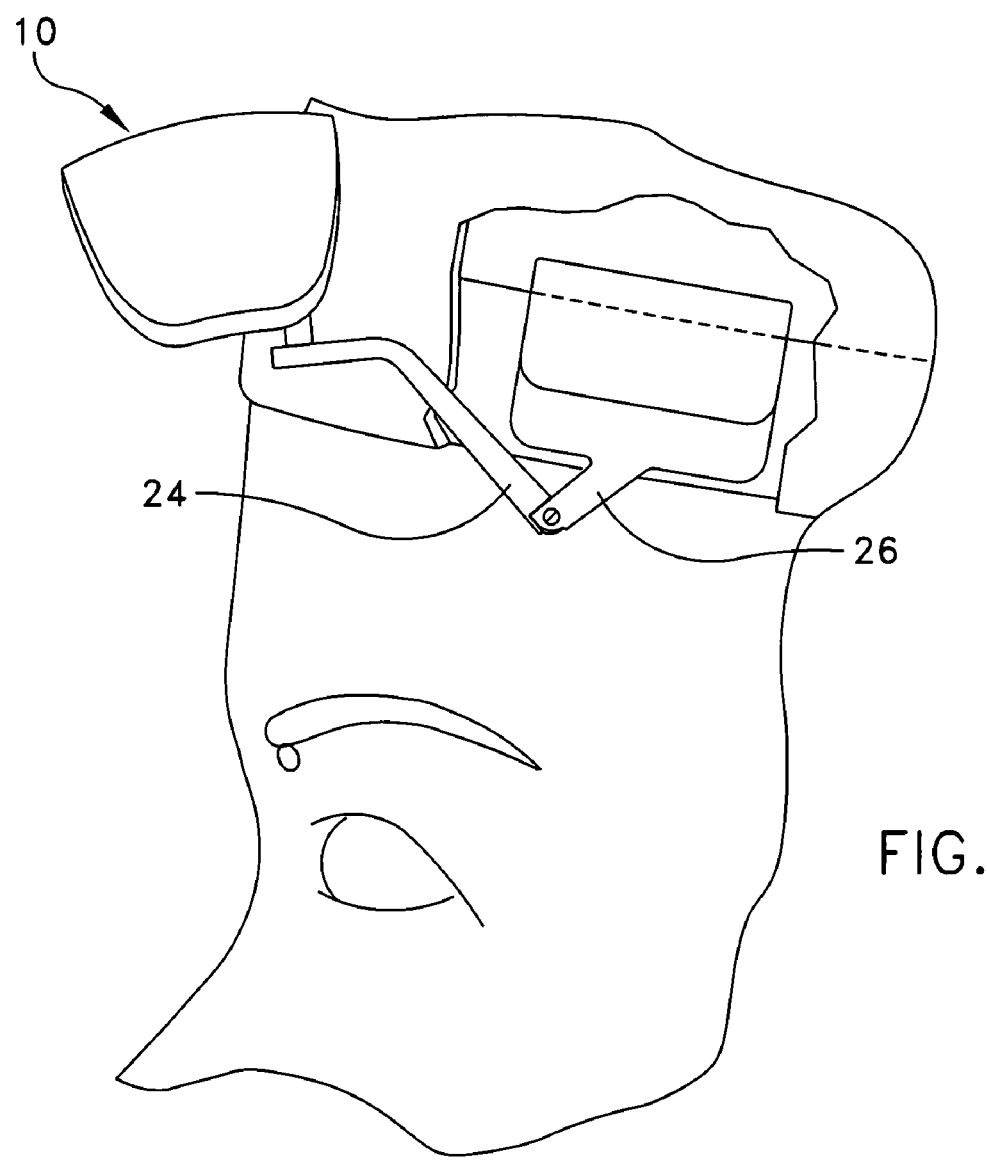
FIG. 14 is a view similar to FIG. 12 with the eyeglasses pivoted upward in their storage position.
Figure 15:
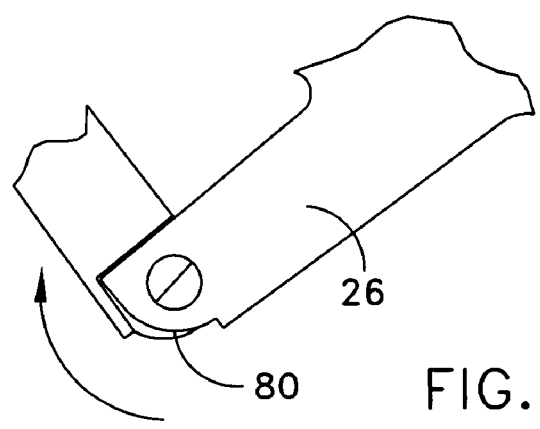
FIG. 15 is a detailed view of FIG. 14.
Figure 16:
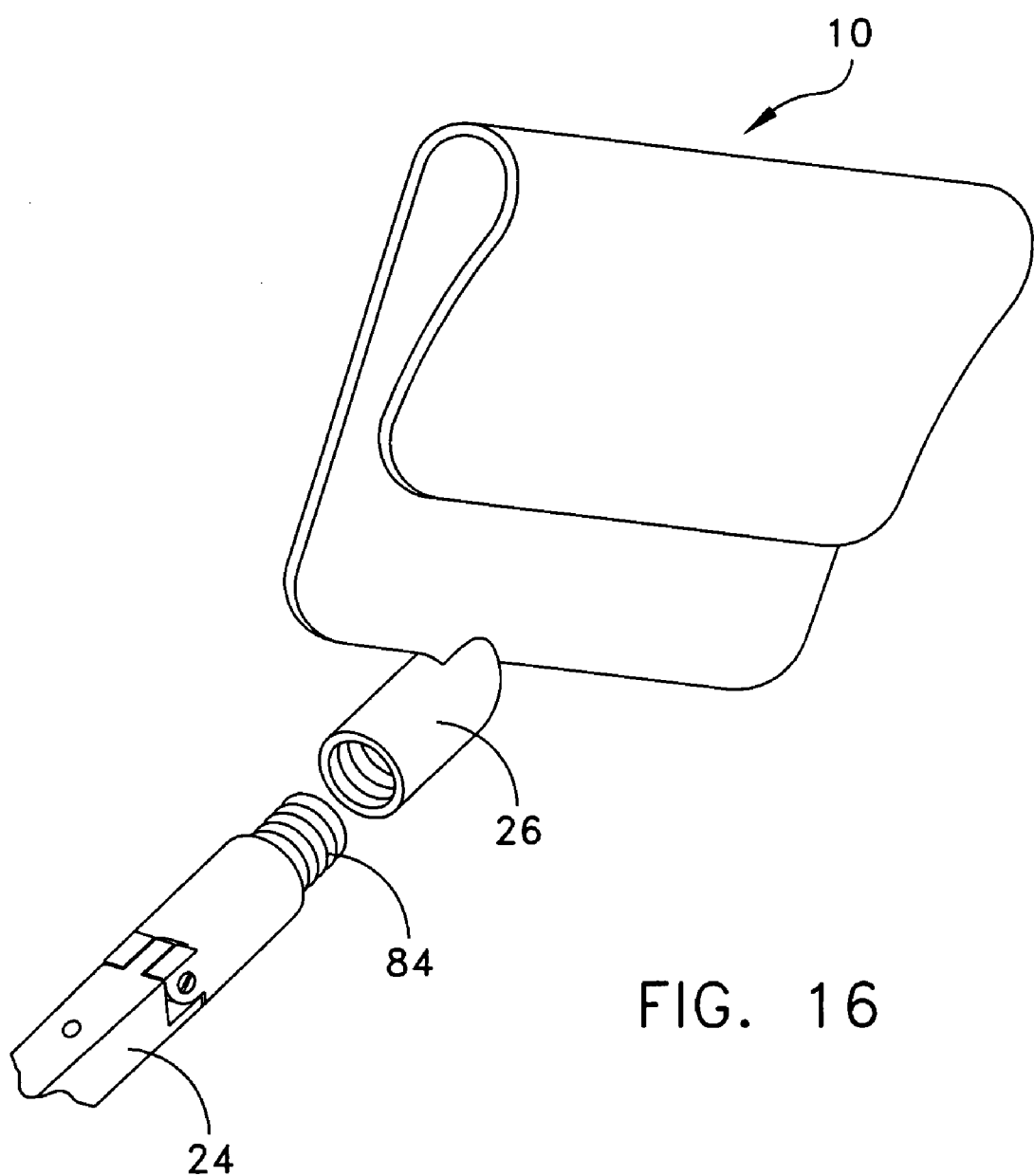
FIG. 16 is a detailed view of a modified form of securing the eyeglass temple to the attaching portions.

The connection between the portions 24, 26 includes a spring feature in the form of a bifurcated tongue 70 on the terminal end of the rearward temple portion adopted to engage a tongue 72 extending from the main temple portion 73. Both tongues 70, 72 have aligned openings 74, 76 respectively, and one of the tongue openings 74 is threaded such that a screw 78 may be used to attach the temple portions together. The terminal ends of the tongues 70 include curved ramps 80 which, in effect, form a spring engagement with the stopping surfaces 82 formed at the end of the main temple portion 24. In this way, the temple portions may be snapped approximately 90 degrees between alternate positions with respect to each other to create the use and storage positions of the glasses as shown in FIGS. 12 and 14 respectively. Also as shown in FIG. 16, the rearward temple portion may be attached to the connecting portion 60 via a threaded coupling 84 shown therein as an alternate feature.

Figure 17:
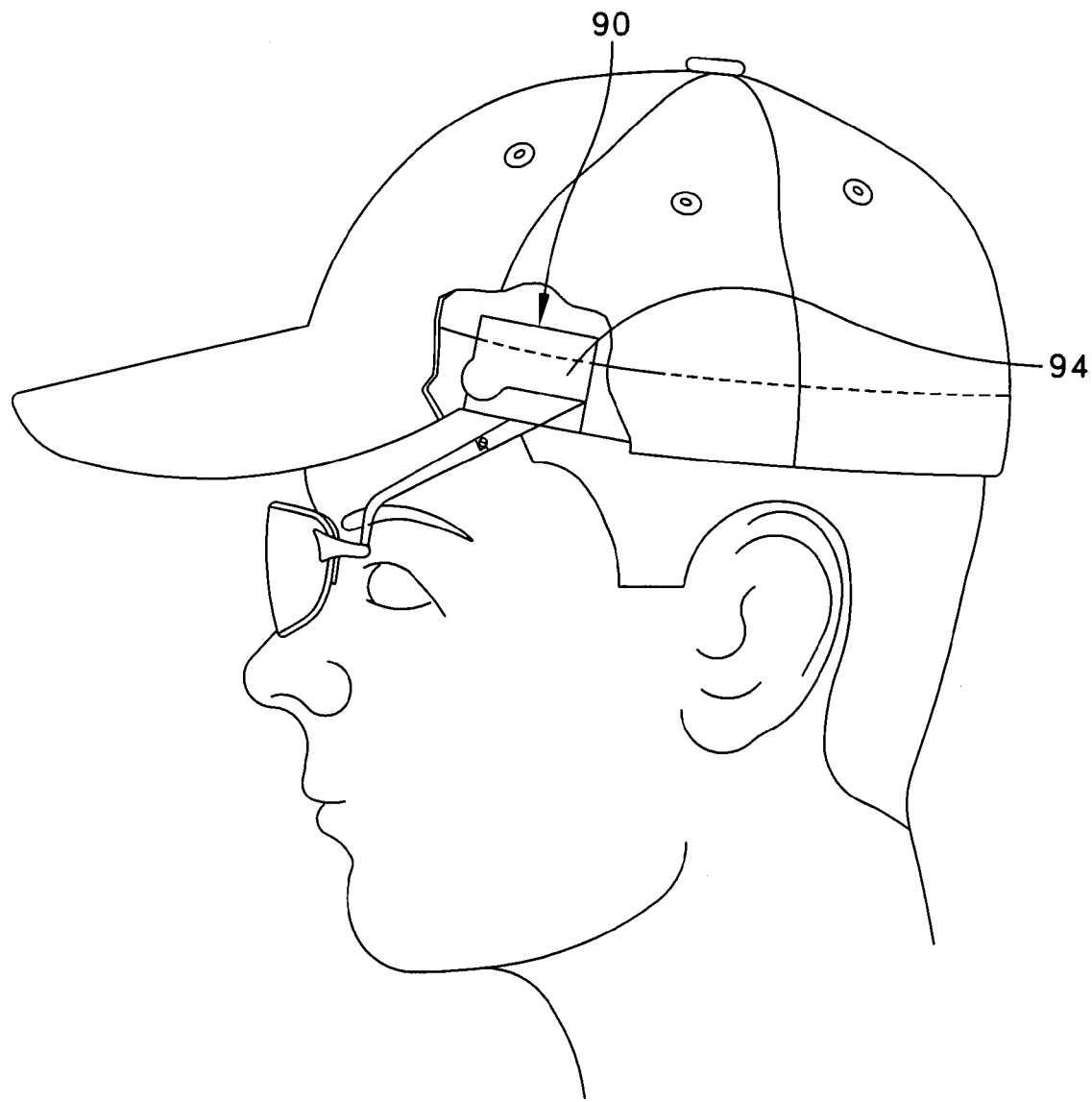
FIG. 17 is a side elevational view similar to FIG. 4 but showing the glasses mounted to the cap with the cap positioned in the forward facing position and wherein a modified version of the attaching portions shown in FIG. 10 are shown.
Figure 18:
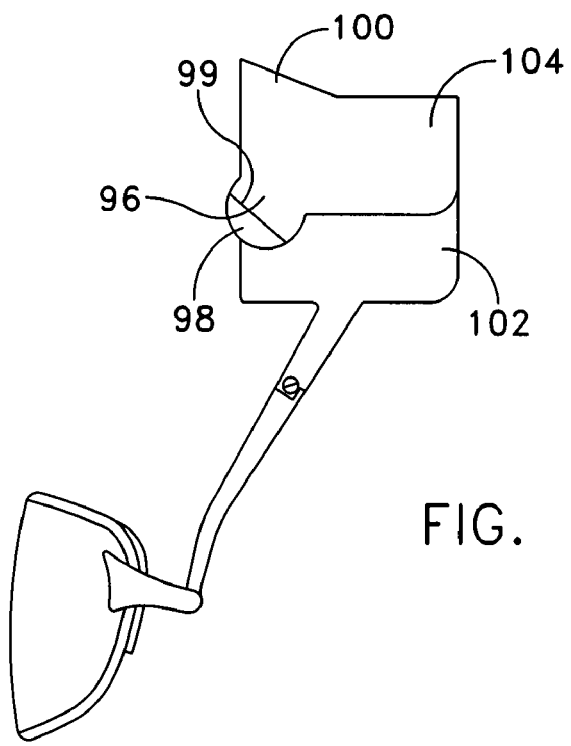
FIG. 18 is a side view of the device shown in FIG. 17 wherein the pivot is in its downwardly extended use position.
Figure 19:
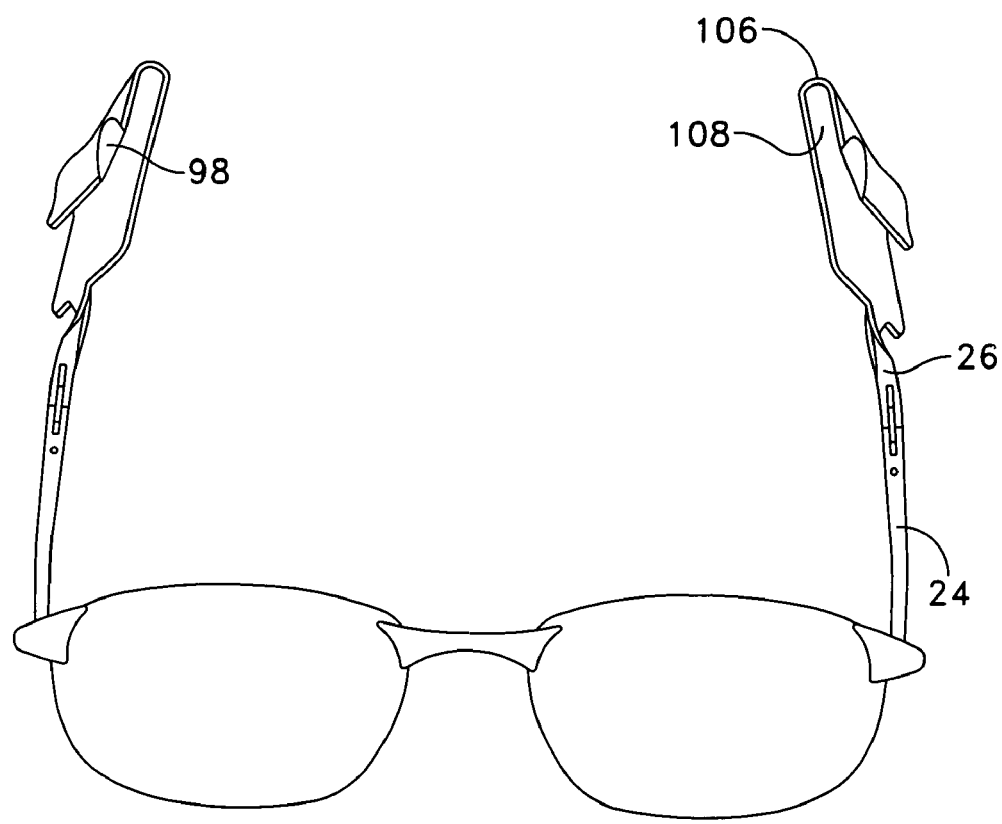
FIG. 19 is a top perspective view of FIG. 18.
Figure 22:
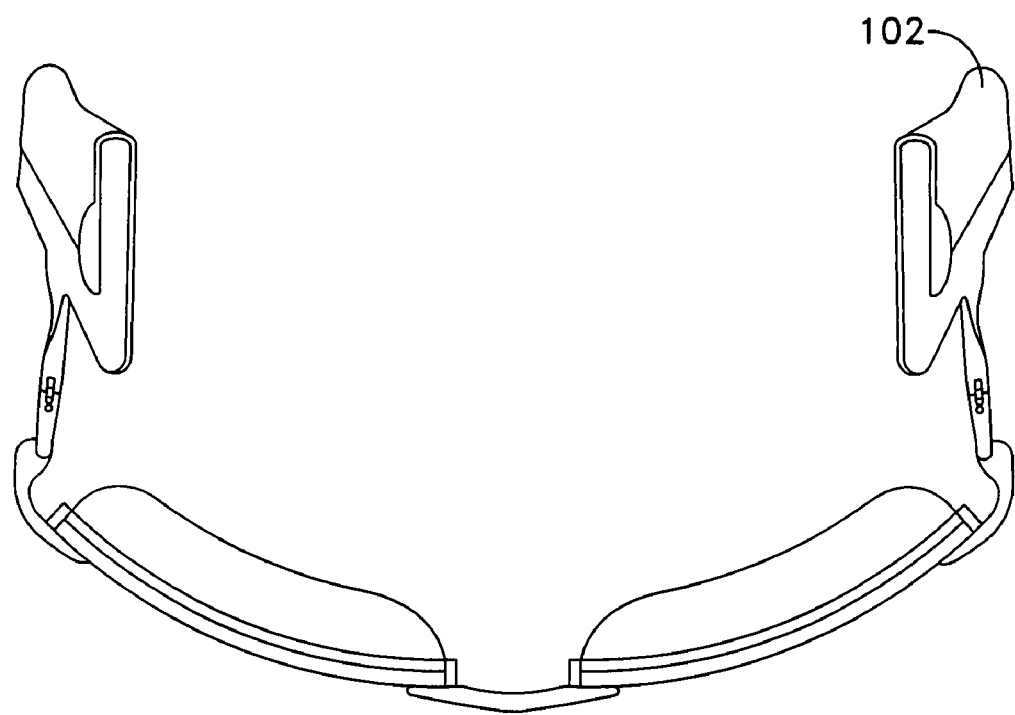
FIG. 22 shows a top perspective view of the glasses shown in FIG. 17 and illustrating a further embodiment of the attaching portions which include an outwardly bent tip and wherein the temples are in the upward pivoted position.
Figure 20:
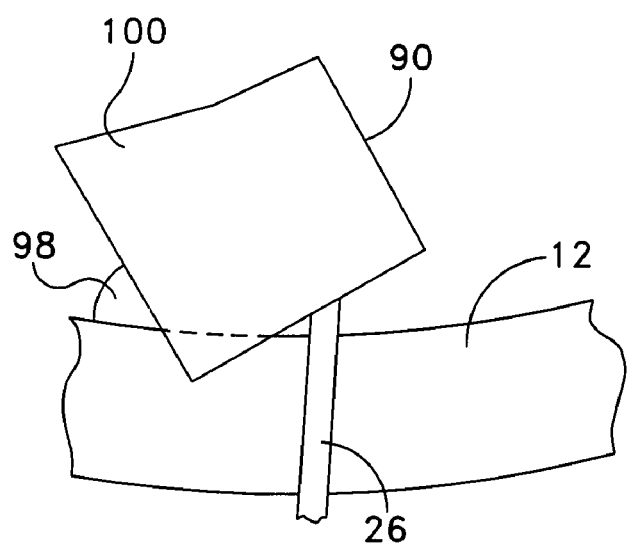
FIG. 20 is a partial side view of an attaching portion of FIG. 18 as it is moved over the top or terminal edge of the cap inner band.
Figure 21:
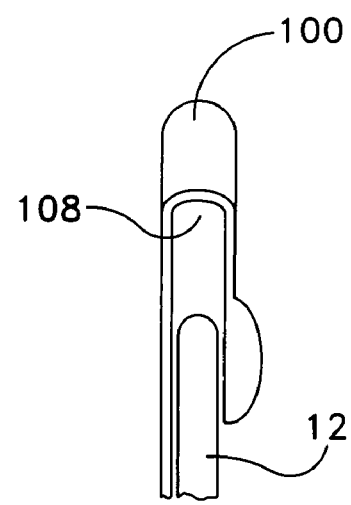
FIG. 21 is a rear elevational view showing how the outwardly bent lip provides a lead into the internal groove of the attaching portion.

The previous discussion in relation to FIGS. 1-16 primarily focused on utilizing the glasses and their mounting system when wearing the cap in the backwards position, that is, with the brim or visor positioned to the rear. FIGS. 17-26 depict the mounting system with the brim facing forward, but it should be recognized that the structural features discussed can be equally utilized when the cap is worn facing rearward, that is, with the brim or visor portion facing rearward. FIG. 17 shows the glasses 10 mounted to the headband 12 of the cap 13 via a modified form of connecting portions 90 similar to connecting portions 60 as shown in FIGS. 10-16 but wherein the outer flange 94 of the connected flanges 92, 94 is provided with a generally circular tab 96 extending from the lower portion of the inner flange 92 and including a forwardly extending lateral edge surface 98. The tab 96 is outwardly bent along line 99 and thus surface 98 serves as a lead-in similar to lead-in 42 but extending from the forward lateral edge rather than the bottom edge of the flange. In this manner, the lead-in tabs 96 are positioned in a downward attitude when the glasses are in their extended position shown in FIGS. 18, 19 and positioned essentially within the cap and above the hat or cap band 12 as depicted in FIGS. 20 and 21.

Figure 23A:
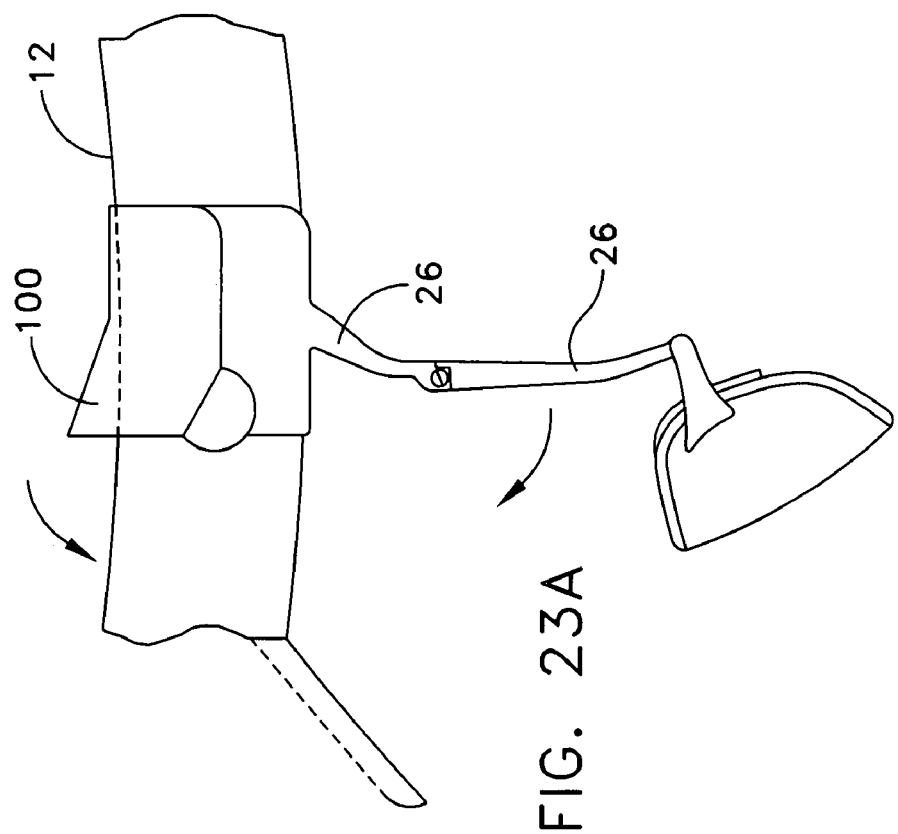
FIG. 23A is a side elevational view of the device shown in FIG. 21 but showing one of the attaching portions of the device mounted to the inner brim of a cap and positioned with the cap brim or bill in the forward facing position.
Figure 23B:
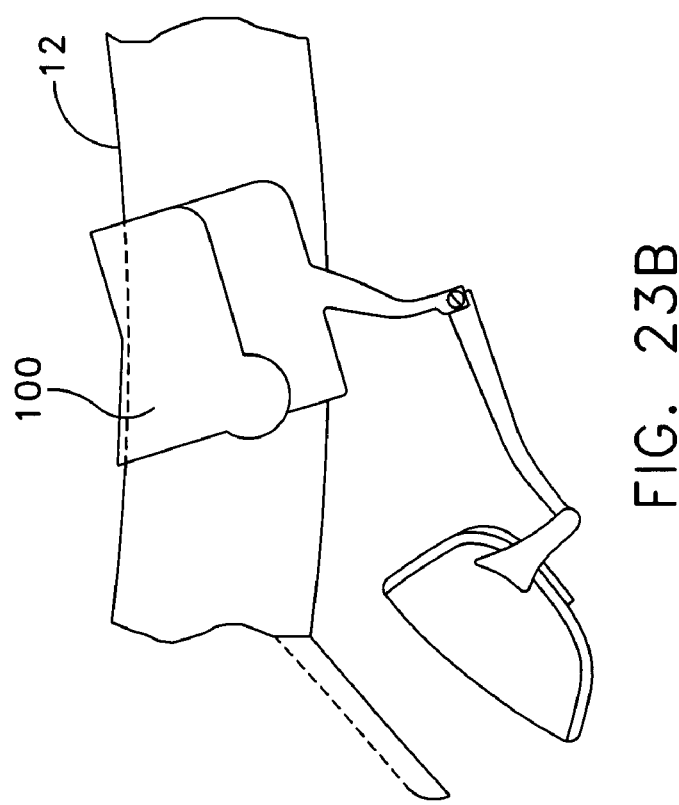
FIG. 23B is a view similar to FIG. 23A but showing the progressive movement of the device when it is upwardly pivoted to the storage position.

A further important constructional feature is the inclusion of a ramp 100 forwardly upwardly extending in the U-shaped bend 106 that connects the inner flange 102 to the outer flange 104 which forms the grooves 108 into which the opposite sides of the headband are received. Since caps vary to a considerable extent, their brims can be positioned at various angles to the cap portion. In some cases, the brim is angled downwardly from the cap such that inner surface portions thereof are contacted by the glasses when they are pivoted to their storage position beneath the rim. The transition between FIGS. 23A and 23B shows how this undesirable contact may be prevented by the ramp 100. Therein, the ramp 100 enables the connecting portions 90 to rock forwardly to a position where the inner surface of the ramp contacts the upper edge of the band and in that way rearwardly shifts or, in effect, lowers the position of the upwardly pivoted glasses so such that the glasses will not contact the brim undersurfaces. Thus in FIG. 23A, the rear portions of the groove firmly contact the upper edge of the band 12 and tend to stabilize the positioning of the connecting portions; and when the device is upwardly pivoted in the direction of the arrows shown in FIG. 23A, that contact with the upper band edge shifts to that portion of the receiving groove defined by the undersurface areas of the ramp 100.

Figure 26:
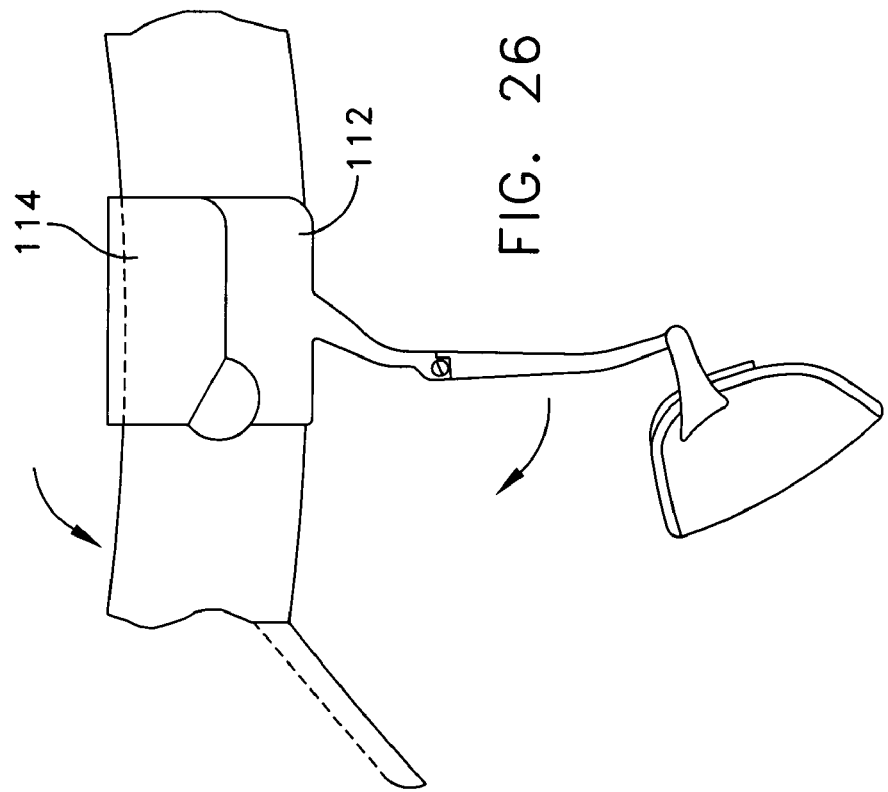
FIG. 26 is a view similar to FIG. 25 but showing the movement of the device in the direction of the arrows shown in FIG. 25.
Figure 25:
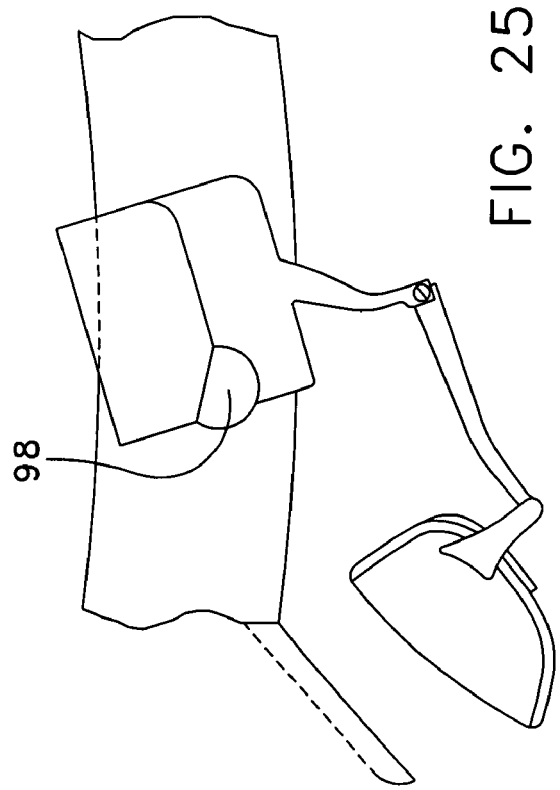
FIG. 25 is a side elevational view similar to FIG. 23A but featuring the rockable attaching portion of FIG. 24.
Figure 24:
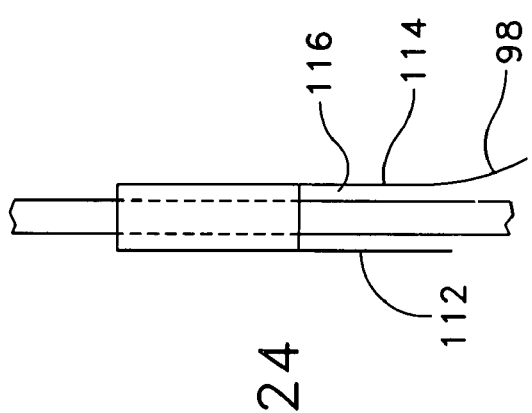
FIG. 24 is a top view similar to FIG. 21 but showing a further rockable attaching portion embodiment.
Figure 28:
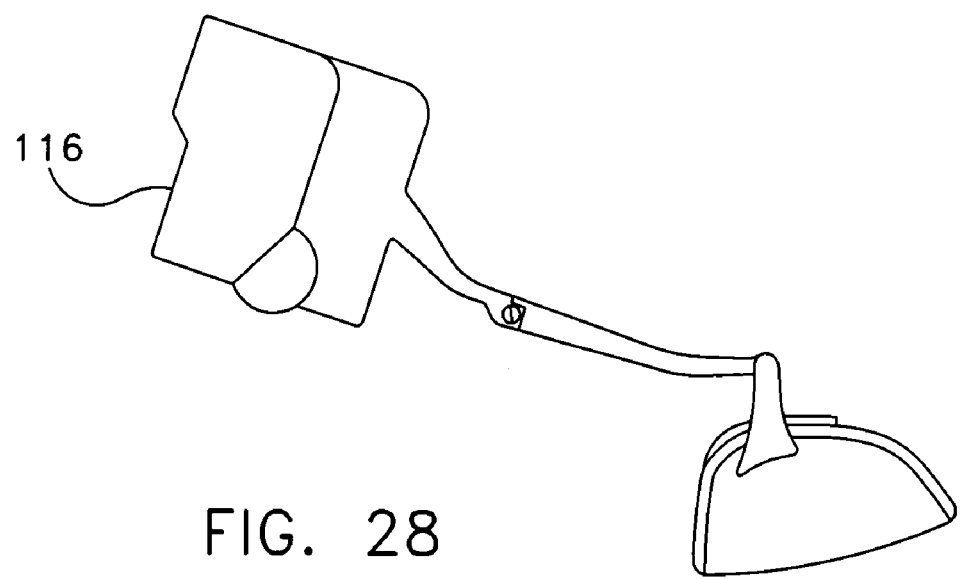
FIG. 28 is a side elevational view of FIG. 24.
Figure 27:
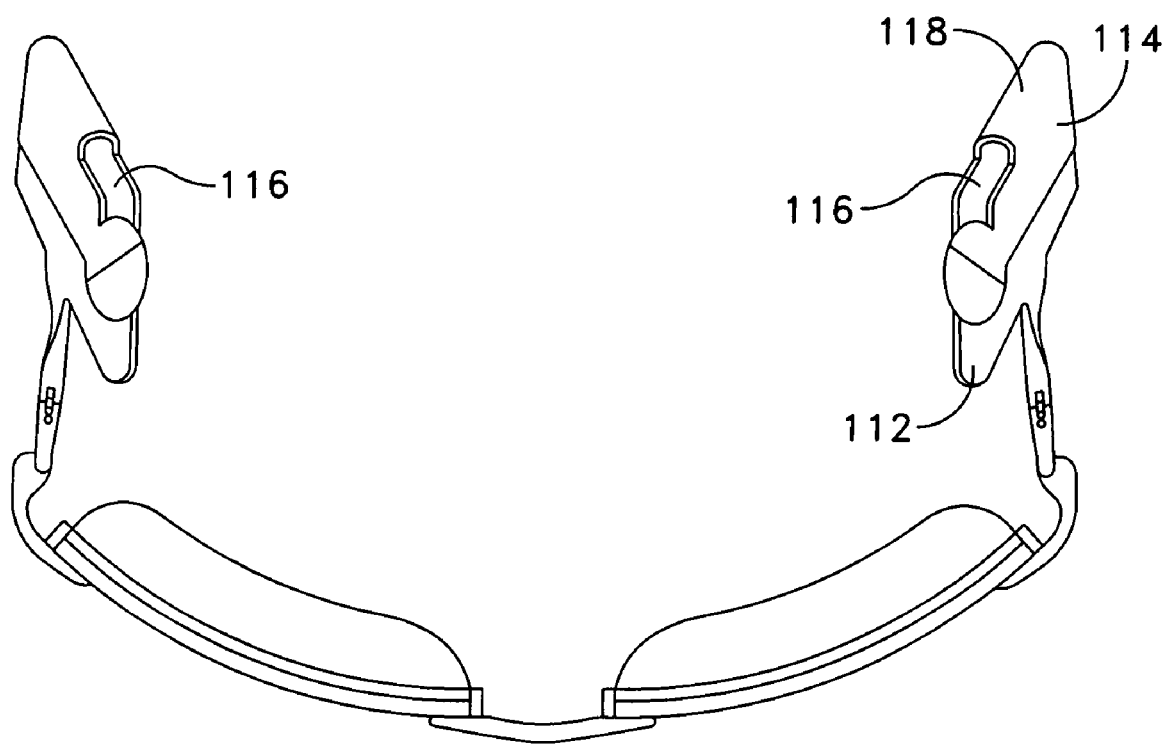
FIG. 27 is a top perspective view of FIG. 25.
Figure 29:
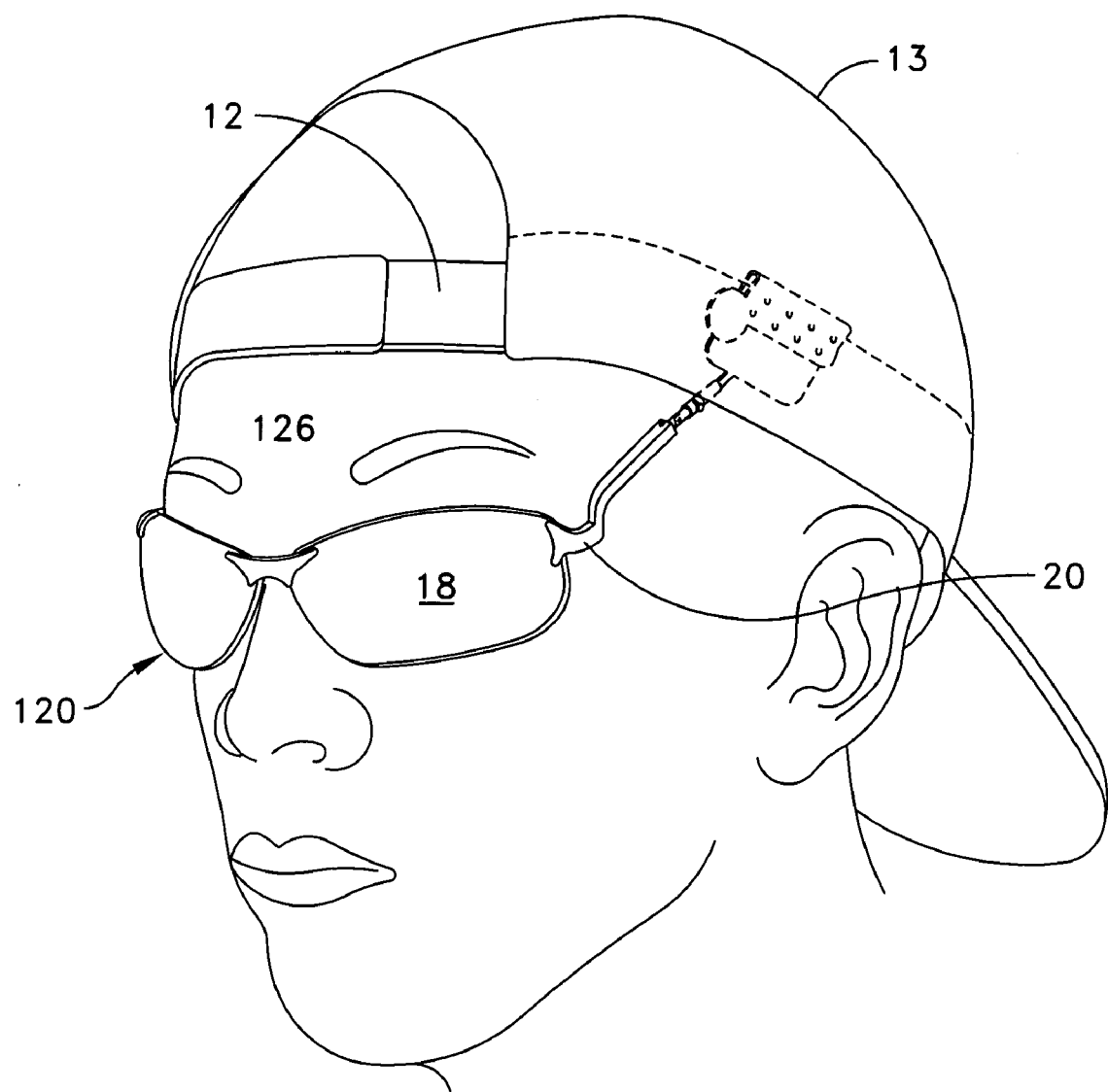
FIG. 29 is a front perspective view similar to FIG. 1 but showing a modified form of the glasses wherein the connecting portions are partially rotatable to assist in donning the glasses.
Figure 30:
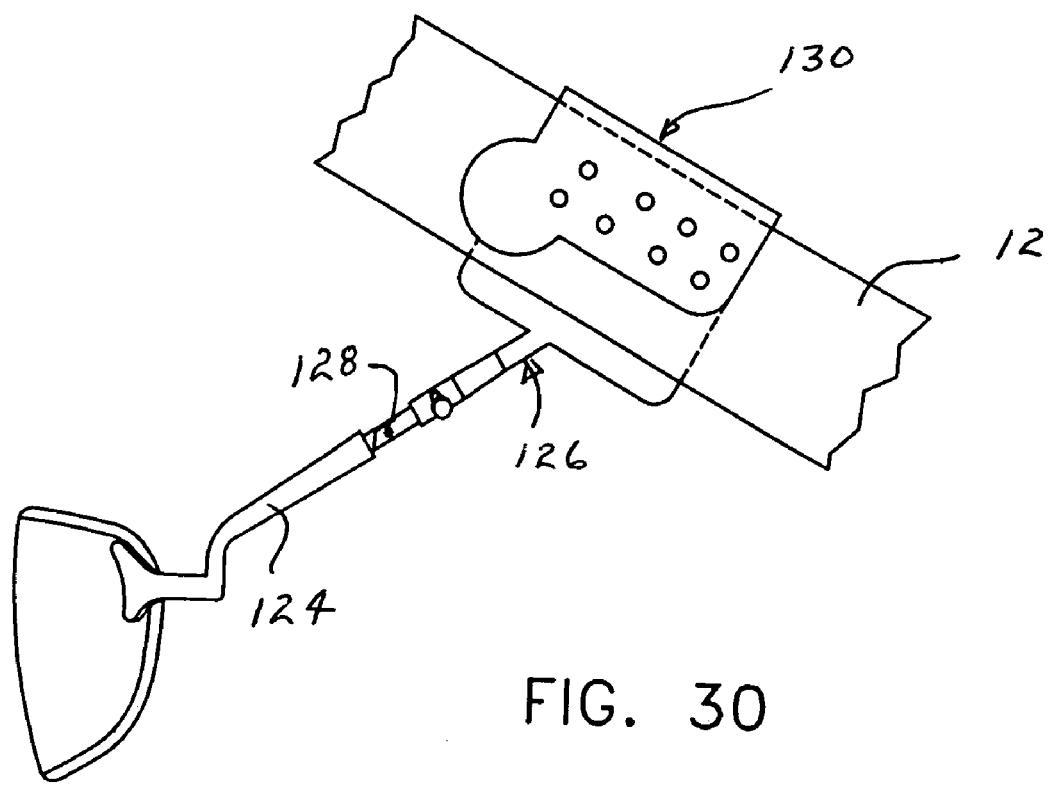
FIG. 30 is a side elevational view of the glasses of FIG. 29 showing the temples in a straight mounting position.
Figure 31:
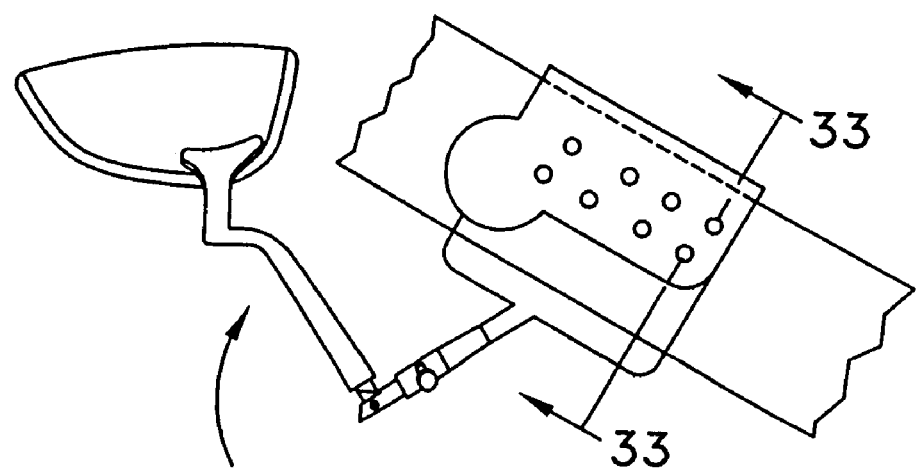
FIG. 31 is a side elevational view similar to FIG. 30 but with the forward portions of the temples upwardly pivoted to a storage position.

A further variation of this rocking action to facilitate increased clearance between the glasses and the brim when the glasses are in the upwardly pivoted storage position and the cap is positioned facing forwardly is shown in FIGS. 24, 25 and 26. Therein, the forward portion of the U-shaped bend that connects the inner and outer flanges 112 and 114 of the connecting portions 110 are cut away to form a cut-out 116 such that the flanges 112, 114 are connected solely by the web 118. In this manner, the connecting portions are able to rock forwardly downwardly in a manner similar to that depicted by FIGS. 23A, 23B. It should be pointed out that there would be less contact between the groove formed solely by the contact between the undersurfaces of the flanges 112, 114 and the cap band than in the previous embodiment; however in both embodiments, the position of the glasses in both the operative and storage positions is to a large extent brought about by the side to side frictional contact between the cap band and the flanges as these components are, in effect, outwardly forced into the cap shell itself by the wearer's head. This frictional contact is, of course, present to an equal extent whether the cap is worn with the brim or visor portion facing forward or backwards, and the rocking features above described are primarily for positioning of the glasses under the cap brim.

Turning now to FIGS. 29-45 of the drawings, a modified form of the invention is shown which has certain advantages over the previously described embodiments. With such previously described embodiments, some degree of skill in orienting the flanges in attaching the glasses to the cap headband was desirable, and the modified forms shown in FIGS. 29-45 simplify the process.

The glasses 120 of the modified form of the present invention are depicted in a position mounted to the inner headband 12 of a cap 13. The glasses 120 include a frame preferably of one-piece anodized aluminum or other suitable material that in turn supports a pair of eyepieces 18 by conventional means such as the rivets 20. Temples 122 are disposed at the lateral ends of the frame. The temples include forward or main temple portions 124 which rearwardly extend from the frame and are, in turn, connected at their ends 125 to rearwardly extending temple portions 126 via a pivot connection 128. The rearward extending portions of the temples 122 in turn each terminate in a connecting or attaching portion 130.

The temple connecting portions 130 or flange pair include an inner flange 132, that is, an extension of the rearward temple portion 126, and an outwardly positioned flange 134 separated therefrom and connected thereto by a U-shaped bend or web 136. The band 12 generally comprises a vertically oriented circumferentially extending fabric which is often the upturned periphery of the cap top 14 and includes a terminal edge 15 over which a receiving groove 138 extends. The outer wall or flange 134 may also be outwardly offset at its lower terminal portion 142 to form a lead-in to facilitate the receipt of the band 12.

In the embodiments of FIGS. 29-45, the rearward temple portion is partially rotatable back ad forth about its longitudinal extent so as to enable the user to better orient the flange pair vis-à-vis the headband for attaching the glasses to the cap especially when one of the flange pairs has been connected and the alignment of the other flange pair is not exactly positioned for a variety of reasons, e.g., glasses are tilted, cap is crooked, etc. Thus, the rearward temple portion 126 is generally made up of a two-part shaft 150 with a forward shaft part 152 connected to a terminal shaft part 154 and interconnected for limited twisting rotation with respect to each other.

Figure 35:
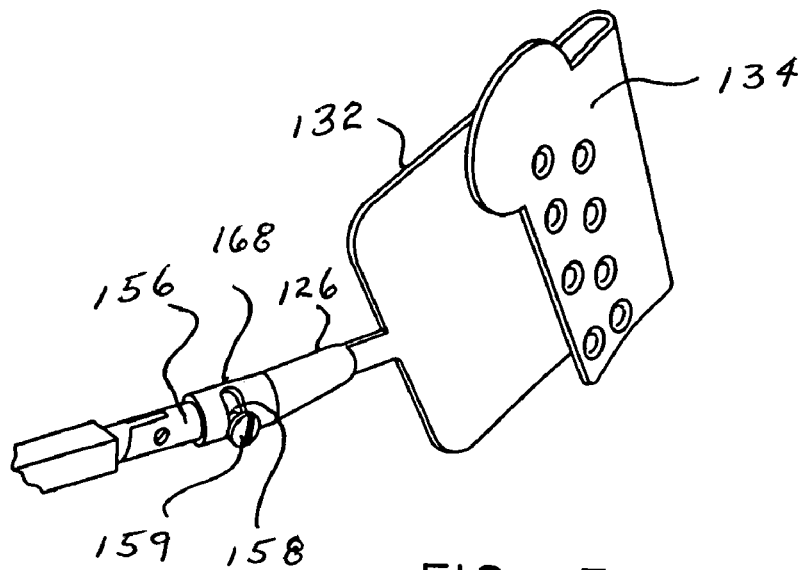
FIG. 35 is an enlarged partial perspective view of FIG. 30 showing the connecting portion in an intermediate rotational position.
Figure 36:
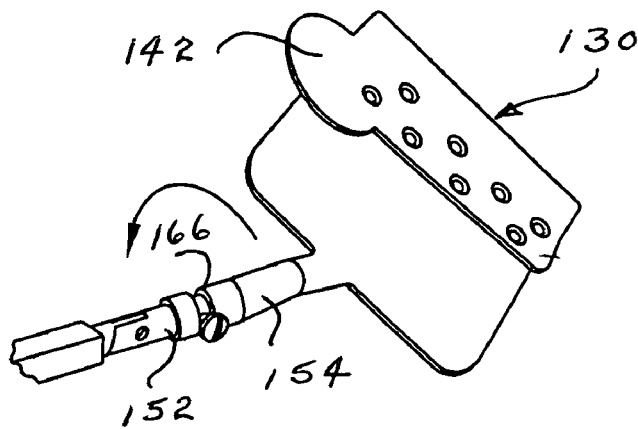
FIG. 36 is a view similar to FIG. 35 but showing the connecting portion rotated to the full extent in one direction.
Figure 37:
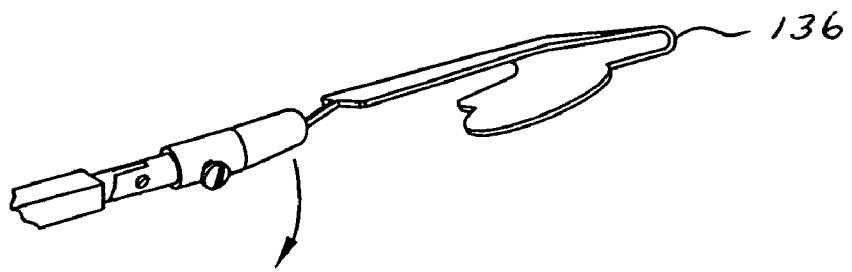
FIG. 37 is a view similar to FIG. 35 but showing the connecting portion rotated to the full extent in the opposite direction from that shown in FIG. 36.
Figure 38:
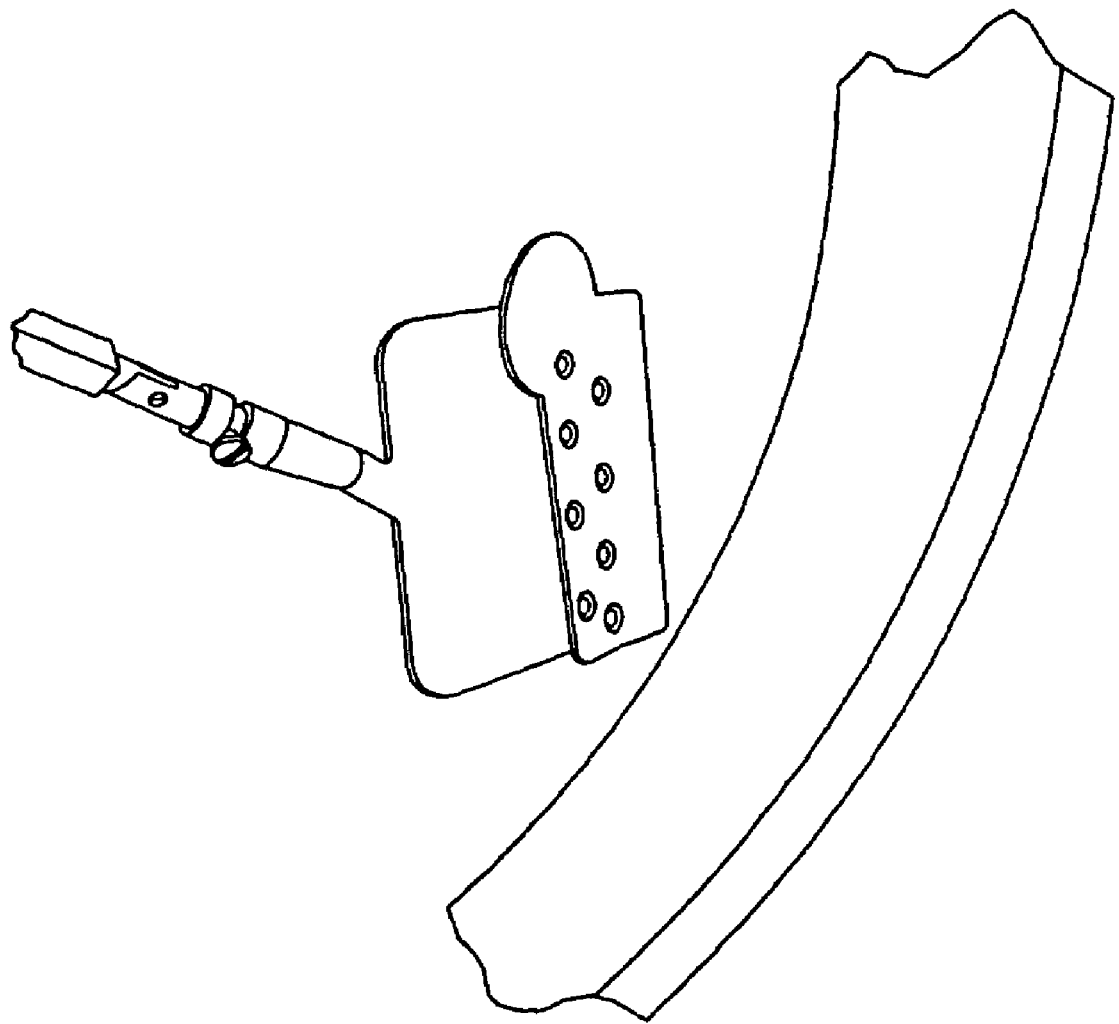
FIG. 38 is a partial exploded view showing the connecting portion disposed in proximity of the cap headband.
Figure 39:
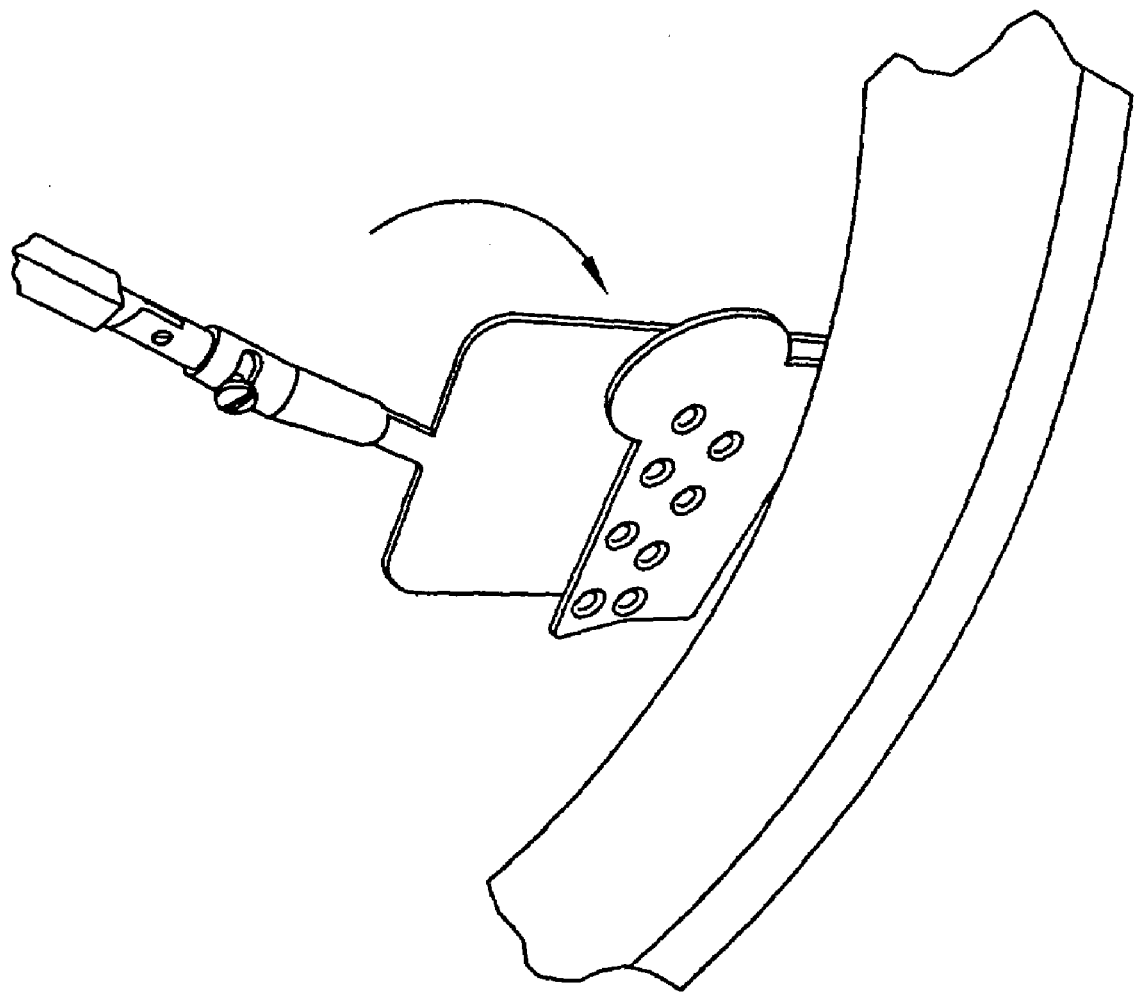
FIG. 39 is a partial exploded view similar to FIG. 38 but showing the connecting portion rotated to a position aligned with the headband for mounting relationship therewith.
Figure 40:
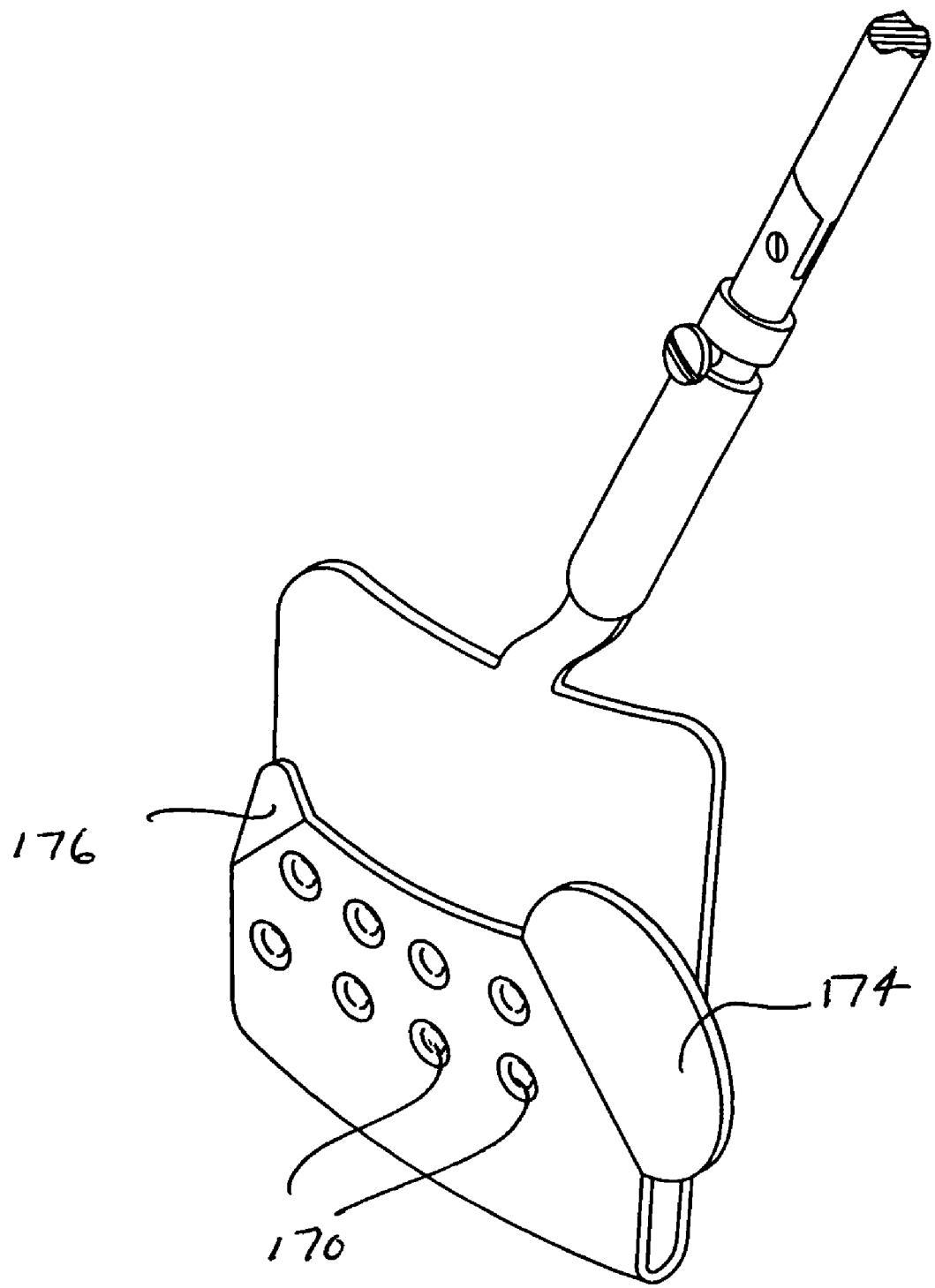
FIG. 40 is a view similar to FIGS. 38 and 39 but without the to headband and illustrating a variation in the construction of the outer flange.
Figure 41:
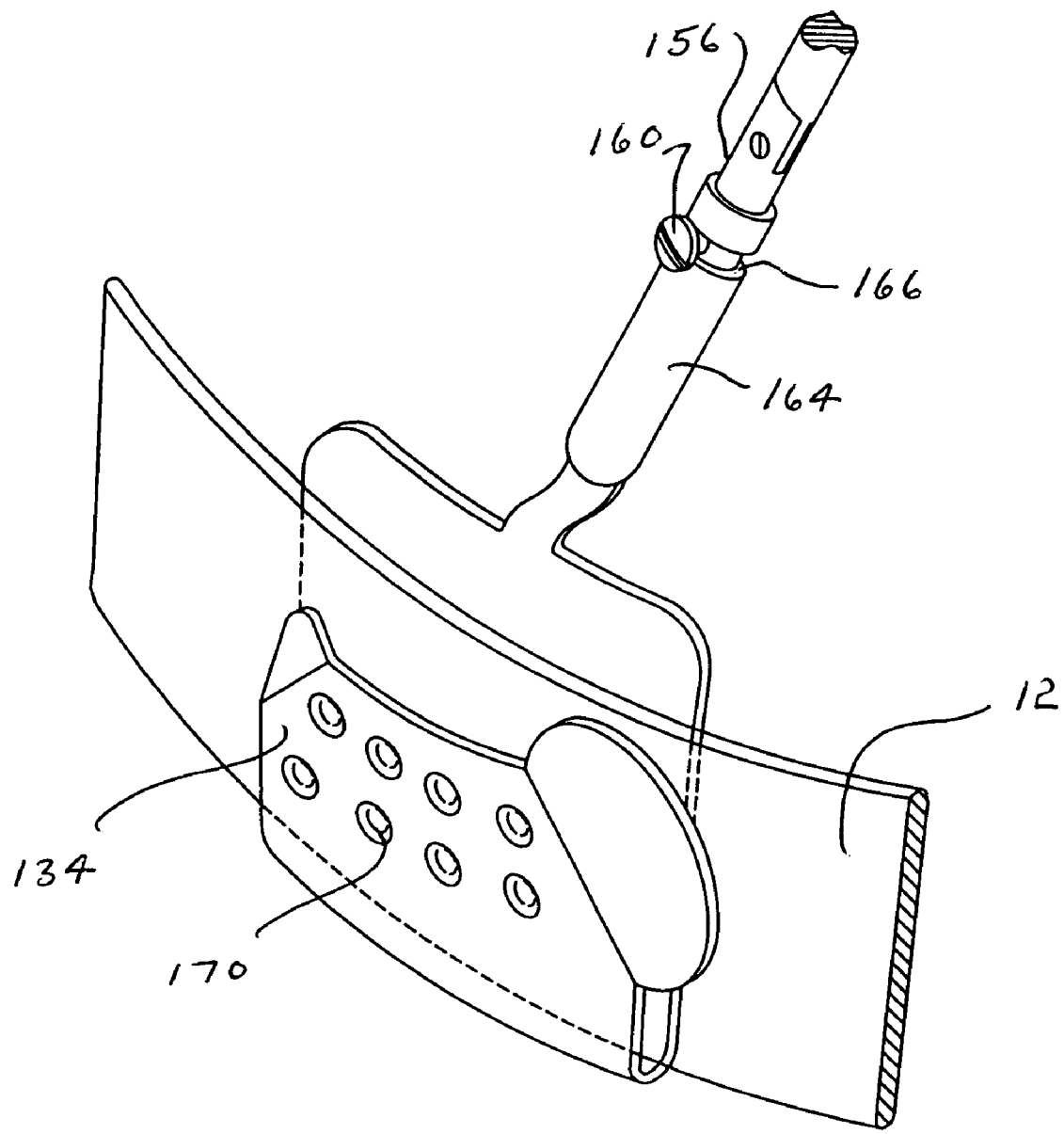
FIG. 41 is a view similar to FIG. 40 showing the headband and the positioning of the flange pair in the mounted position.
Figure 45:
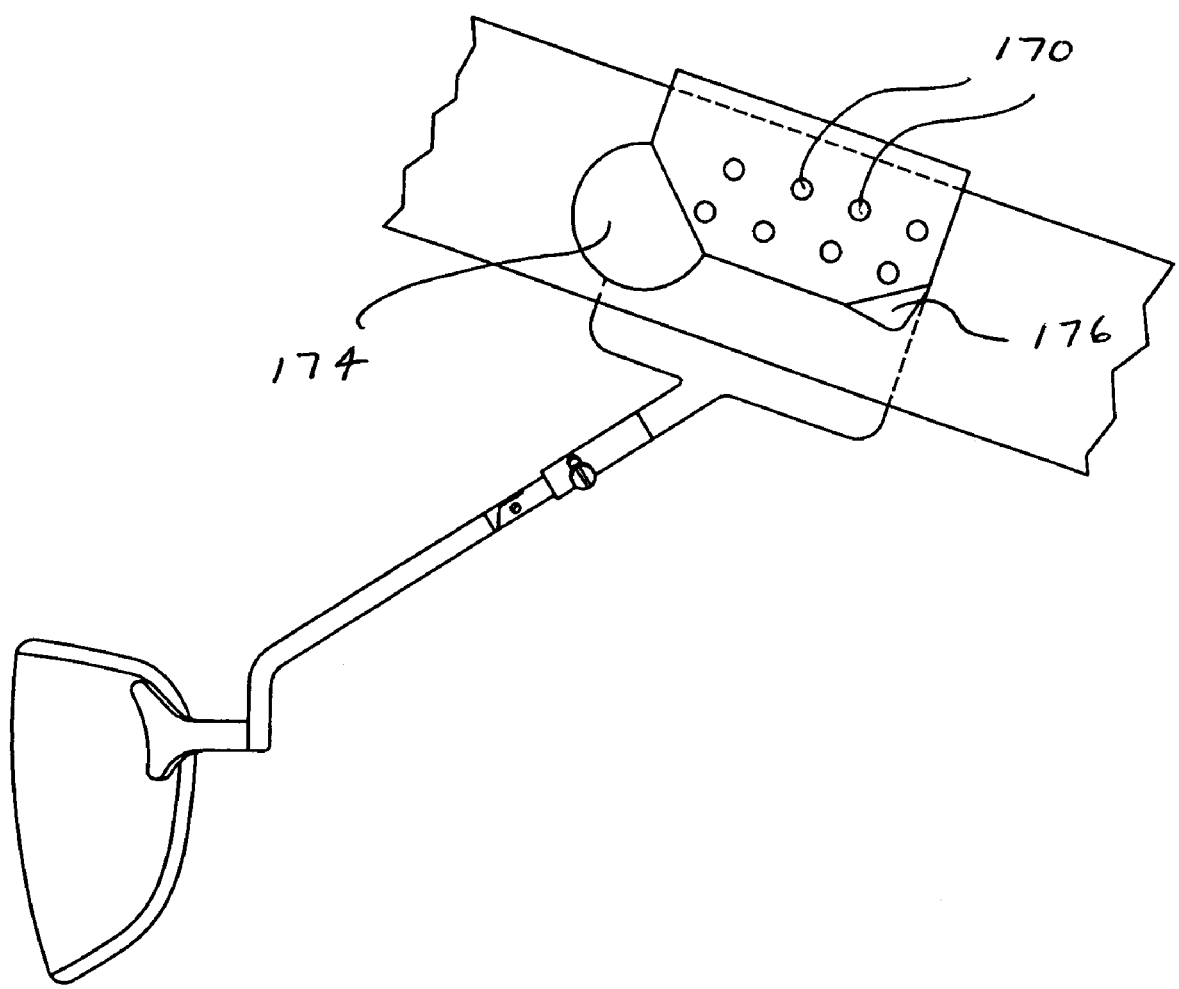
FIG. 45 is a view similar to FIG. 41 of the glasses attached to the headband and with the remaining portions of the cap removed for clarity of illustration.

As best illustrated in the sequence shown in FIGS. 35-37, the forward shaft part is pivotally connected to the forward temple portion as in the other embodiments. Such forward shaft part comprises a stub potion 156 having a threaded bore 158 adapted to receive a friction adjusting screw 159 preferably having a head 160 with a flat undersurface 162. The terminal shaft part 154 is connected at one end to the flange pair 130 and configured at its opposite end in a connecting means such as a hollow boss or tube 164 into which the stub 156 may be received. The tube 164 includes a slotted opening 166 of less than 360 degrees extent and may be formed via a connecting web 168. Once the stub is inserted into the tube, they are oriented so the threaded bore lies below the slotted opening 166 and there the screw is engaged with the bore so as to connect the two shaft parts for rotational movement back and forth along the longitudinal extent thereof. By adjusting the screw 159, the ease of rotation can be controlled or even their positions fixed if desired.

The above described rotational movement better enables one to position the flange pairs over the headband for receipt of the headband therein at the two circumferentially spaced positions for mounting. Also as the separate flange pairs are independently capable of relative rotation about their respective shaft parts, one flange pair may be more readily initially positioned over the headband and thereafter the second remaining flange pair positioned which procedure is often desirable in the donning or mounting process.

The above described procedure is especially desirable when, as shown in FIGS. 29-45, one of both of the flanges 132 and 134 may be provided with friction enhancing means, e.g., in the form of protuberances 170 punched or otherwise formed preferably in the outer flange 134. For instance, in the forming process the flange 134 can be punched such that openings 172 with relatively sharp protuberances 170 extending into the interior space between the flanges can enhance the holding force by frictionally gripping the headband portion positioned therebetween, and may even enable a relatively fixed positioning of that flange pair onto the cap. In those situations, it is even more desirable to have the other temple connection rotatable to assist in mounting the other flange pair to the headband.

Furthermore, as shown in FIGS. 41-45, the outer flange 134 may in addition to an outwardly bent tab 174 similar to tab 96 described in the previous embodiments be provided with an inwardly bent tab 176 to provide in addition or in lieu of the protuberances 170 and enhanced gripping force or interference positioning of the headband within the receiving groove 138 formed by the flanges 132, 134.

It should be pointed out that the terms "forwardly", "rearwardly", etc. are dependent on the position of the cap on the wearer's head when so applied.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A combination cap and eyeglass assembly mounted thereon wherein the cap includes a top portion, an upstanding headband having an upper terminal edge and positioned about the bottom inside portion of said top portion and a forwardly extending visor, said eyeglass assembly including glasses in turn including a frame and a pair of temples having forward and terminal ends wherein the forward ends thereof are connected to said frame at opposed laterally spaced locations and said temple terminal ends each terminating in a connecting portion for mounting said eyeglass assembly to the headband of said cap at laterally spaced locations thereof, said connecting portions each including a flange pair comprising an inner flange and an outwardly positioned flange separated therefrom and connected thereto by a generally U-shaped web so as to define a groove between said flanges, each of said grooves positioned over portions of said headband at said opposed laterally spaced locations thereof such that the outer flanges are positioned between and in contact with both said headband and said cap top portion and the inner flanges are positioned and in contact with both said headband and the wearer's head when the cap is positioned on the wearer's head such that the outward force of the wearer's head against the inner flanges stabilizes the position of the connecting portions and that of the glasses, and at least one of said connecting portions including a shaft section with a longitudinally oriented axis and at least partially rotatable back and forth with respect to said longitudinal axis so as to enable adjustment movement of at least one of said flange pairs independent of the glasses.

2. The combination structure of claim 1, wherein both said connecting portions including a longitudinally oriented two-part shaft section wherein said shaft parts of said shaft sections are interconnected for limited twisting rotation including a forward shaft part connected to said temple terminal ends and a terminal shaft part connected to said forward shaft part for relative rotation with respect thereto and said terminal shaft part terminating in said flange pair.

3. The combination structure of claim 2, wherein a force adjustment means to control the relative rotational force between said shaft parts is included.

4. The combination structure of claim 3, including means for connecting said shaft parts together for relative and adjustable rotation comprises one of said shaft parts having a pot and the other of said shaft parts having a sleeve, said sleeve including a radial slot of less than 360 degrees defined by longitudinally spaced edges wherein said post is adapted to extend into said sleeve and wherein said post further includes a threaded bore in turn adapted to receive a headed screw which passes through said slot and extends above said sleeve and in abutting relation to at least one of said slot defining edges, said screw adapted to move in and out of said post threaded bore to control the contact force between said screw head and said sleeve.

5. The combination structure of claim 1, wherein both said connecting portions including a longitudinally oriented two-part shaft section wherein said shaft section wherein said shaft parts are interconnected for limited twisting rotation including a forward shaft part connected to said temple terminal ends and a terminal shaft part connected to said forward shaft part for relative rotation with respect thereto and said terminal shaft part terminating in said flange pair.

6. The combination structure of claim 5, wherein both of said flange pairs include said friction enhancing means.

7. The combination structure of claim 5, wherein said friction enhancing means is a plurality of protuberances inwardly extending from at least one of said flange pairs into contact with said headband.

8. The combination structure of claim 1 wherein each of said temples include a forward portion connected to said eyeglass frame and a rear portion connected to said forward portion by a pivotable hinge such that said forward portions are upwardly pivotable above said rear portions approximately 90 degrees so as to move said frame from a use position to a storage position while maintaining the attachment between said headband and said connecting portions.

9. An eyeglass assembly adapted for mounting to either the front or rear of a cap having a top portion, an upstanding headband having an upper terminal edge and positioned about the bottom inside portion of said top portion and a forwardly extending visor, said eyeglass assembly including glasses in turn including a frame and a pair of temples having forward and terminal ends wherein the forward ends thereof are connected to said frame at opposed laterally spaced locations and said temple terminal ends each terminating in a connecting portion for mounting said eyeglass assembly to the headband of said cap at laterally spaced locations thereof, said connecting portions each including a flange pair comprising an inner flange and an outwardly positioned flange separated therefrom and connected thereto by a generally U-shaped web so as to define a groove between said flanges, each of said grooves positioned over portions of said headband at said opposed laterally spaced locations thereof such that the outer flanges are positioned between and in contact with both said headband and said cap top portion and the inner flanges are positioned and in contact with both said headband and the wearer's head when the cap is positioned on the wearer's head such that the outward force of the wearer's head against the inner flanges stabilizes the position of the connecting portions and that of the glasses, wherein each of said temples include a forward portion connected to said eyeglass frame and a rear portion connected to said forward portion by a pivotable hinge such that said forward portions are upwardly pivotable above said rear portions approximately 90 degrees so as to move said frame from a use position to a storage position while maintaining the attachment between said headband and said connecting portion and at least one of said connecting portions including a shaft section with a longitudinally oriented axis and at least partially rotatable back and forth with respect to said longitudinal axis so as to enable adjustment movement of at least one of said flange pairs independent of the glasses.

10. The eyeglass assembly of claim 9, wherein both said connecting portions including a longitudinally oriented two-part shaft section wherein said shaft section wherein said shaft parts are interconnected for limited twisting rotation including a forward shaft part connected to said temple terminal ends and a terminal shaft part connected to said forward shaft part for relative rotation with respect thereto and said terminal shaft part terminating in said flange pair.

11. The eyeglass assembly of claim 9, wherein both said connecting portions including a longitudinally oriented two-part shaft section wherein said shaft section wherein said shaft parts are interconnected for limited twisting rotation including a forward shaft part connected to said temple terminal ends and a terminal shaft part connected to said forward shaft part for relative rotation with respect thereto and said terminal shaft part terminating in said flange pair.

12. The eyeglass assembly of claim 9, wherein both of said flange pairs include said friction enhancing means.

13. The eyeglass assembly of claim 9, wherein said friction enhancing means is a plurality of protuberances inwardly extending from at least one of said flange pairs into contact with said headband.

14. The eyeglass assembly of claim 9, wherein a force adjustment means to control the relative rotational force between said shaft parts is included.

15. The eyeglass assembly of claim 14, including means for connecting said shaft parts together for relative and adjustable rotation comprises one of said shaft parts having a pot and the other of said shaft parts having a sleeve, said sleeve including a radial slot of less than 360 degrees defined by longitudinally spaced edges wherein said post is adapted to extend into said sleeve and wherein said post further includes a threaded bore in turn adapted to receive a headed screw which passes through said slot and extends above said sleeve and in abutting relation to at least one of said slot defining edges, said screw adapted to move in and out of said post threaded bore to control the contact force between said screw head and said sleeve.

\* \* \* \* \*